US008460686B2

(12) United States Patent
Clineff et al.

(10) Patent No.: US 8,460,686 B2
(45) Date of Patent: *Jun. 11, 2013

(54) BIOACTIVE BONE GRAFT SUBSTITUTE

(71) Applicant: Orthovita, Inc., Malvern, PA (US)

(72) Inventors: Theodore D. Clineff, Phoenixville, PA (US); Antony Koblish, Malvern, PA (US); Charanpreet S. Bagga, Basking Ridge, NJ (US); Erik M. Erbe, Rancho Santa Fe, CA (US); Gina M. Nagvajara, Narberth, PA (US); Marissa M. Darmoc, Philadelphia, PA (US)

(73) Assignee: Orthovita, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/627,439

(22) Filed: Sep. 26, 2012

(65) Prior Publication Data

US 2013/0059011 A1    Mar. 7, 2013

Related U.S. Application Data

(63) Continuation of application No. 11/771,857, filed on Jun. 29, 2007, now Pat. No. 8,303,967.

(60) Provisional application No. 60/817,617, filed on Jun. 29, 2006.

(51) Int. Cl.
*A61K 9/00* (2006.01)
*A61K 9/14* (2006.01)

(52) U.S. Cl.
USPC ........................................... 424/400; 424/484

(58) Field of Classification Search
None
See application file for complete search history.

(56) References Cited

U.S. PATENT DOCUMENTS

| | | |
|---|---|---|
| 2,920,971 A | 1/1960 | Stookey |
| 3,090,094 A | 5/1963 | Schwartzwalder et al. |
| 3,443,261 A | 5/1969 | Battista et al. |
| 3,679,360 A | 7/1972 | Rubin et al. |
| 3,833,386 A | 9/1974 | Wood et al. |
| 3,877,973 A | 4/1975 | Ravault |
| 3,907,579 A | 9/1975 | Ravault |
| 3,981,736 A | 9/1976 | Broemer et al. |
| 4,004,933 A | 1/1977 | Ravault |
| 4,007,020 A | 2/1977 | Church et al. |
| 4,045,238 A | 8/1977 | Battista et al. |
| 4,149,893 A | 4/1979 | Aoki et al. |
| 4,149,983 A | 4/1979 | Grier et al. |
| 4,273,131 A | 6/1981 | Olsen |
| 4,328,034 A | 5/1982 | Ferguson |
| 4,457,028 A | 7/1984 | Draenert |
| 4,491,453 A | 1/1985 | Koblitz et al. |
| 4,491,517 A | 1/1985 | Janovac |
| 4,563,350 A | 1/1986 | Nathan et al. |
| 4,604,097 A | 8/1986 | Graves, Jr. et al. |
| 4,609,923 A | 9/1986 | Boan et al. |
| 4,612,053 A | 9/1986 | Brown et al. |
| 4,613,627 A | 9/1986 | Sherman et al. |
| 4,619,655 A | 10/1986 | Hanker et al. |
| 4,643,982 A | 2/1987 | Kasuga et al. |
| 4,648,124 A | 3/1987 | Mantovani et al. |
| 4,652,459 A | 3/1987 | Engelhardt |
| 4,652,534 A | 3/1987 | Kasuga |
| 4,673,355 A | 6/1987 | Farris et al. |
| 4,693,721 A | 9/1987 | Ducheyne |
| 4,711,769 A | 12/1987 | Inoue et al. |
| 4,714,721 A | 12/1987 | Franek et al. |
| 4,722,970 A | 2/1988 | Nakagoshi et al. |
| 4,725,234 A | 2/1988 | Ethridge |
| 4,737,411 A | 4/1988 | Graves, Jr. et al. |
| 4,775,646 A | 10/1988 | Hench et al. |
| 4,776,890 A | 10/1988 | Chu |
| 4,780,450 A | 10/1988 | Sauk et al. |
| 4,781,721 A | 11/1988 | Grundei |
| 4,791,939 A | 12/1988 | Maillard |
| 4,803,075 A | 2/1989 | Wallace et al. |
| 4,812,854 A | 3/1989 | Boan et al. |
| 4,849,193 A | 7/1989 | Palmer et al. |
| 4,851,046 A | 7/1989 | Low et al. |
| 4,859,383 A | 8/1989 | Dillon |
| 4,861,733 A | 8/1989 | White |
| 4,868,580 A | 9/1989 | Wade |
| 4,880,610 A | 11/1989 | Constantz |
| 4,888,366 A | 12/1989 | Chu et al. |
| 4,891,164 A | 1/1990 | Gaffney et al. |
| 4,897,250 A | 1/1990 | Sumita |

(Continued)

FOREIGN PATENT DOCUMENTS

| | | |
|---|---|---|
| CA | 2278176 | 7/1998 |
| CA | 2398517 | 8/2001 |

(Continued)

OTHER PUBLICATIONS

Australian Search Report for Application No. 2007265379 dated Dec. 24, 2012.
Australian Search Report for Application No. 2007265379 dated Jan. 7, 2013.
"NovaBone—C/M Synthetic Bone Graft Particulate," POREX Surgical Products Group, 2004, http://www.porexsurgical.com/english/surgical/sprodnova.asp, downloaded from internet on Aug. 22, 2007.
Abbona et al., "Crystallization of Calcium and Magnesium Phosphates from Solutions of Medium and Low Concentrations," Cryst. Res. Technol., 1992, 27, pp. 41-48.
Allan I, Newman H, Wilson M. Antibacterial activity of particulate Bioglass against supra- and subgingival bacteria. Biomaterials 2001; 22:1683-1687.
Allan I, Newman H, Wilson M. Particulate Bioglass reduces the viability of bacterial biofilms formed on its surface in an in vitro model. Clin OralImpl Res 2002; 13:53-58.

(Continued)

Primary Examiner — Scott Long
Assistant Examiner — Lyndsey Beckhardt
(74) Attorney, Agent, or Firm — Lerner, David, Littenberg, Krumholz & Mentlik, LLP

(57) ABSTRACT

The invention relates to biocompatible bone graft materials for repairing bone defects and the application of such bone grafts. The devices of the invention comprise resorbable calcium phosphate, resorbable collagen and bioactive glasses.

20 Claims, 33 Drawing Sheets

U.S. PATENT DOCUMENTS

| | | | |
|---|---|---|---|
| 4,927,866 A | 5/1990 | Purrmann et al. |
| 4,983,573 A | 1/1991 | Bolt et al. |
| 4,988,362 A | 1/1991 | Toriyama et al. |
| 5,034,352 A | 7/1991 | Vit et al. |
| 5,047,031 A | 9/1991 | Constantz |
| 5,053,212 A | 10/1991 | Constantz et al. |
| 5,108,436 A | 4/1992 | Chu et al. |
| 5,112,354 A | 5/1992 | Sires |
| 5,129,905 A | 7/1992 | Constantz |
| 5,134,009 A | 7/1992 | Ichitsuka et al. |
| 5,204,106 A | 4/1993 | Schepers et al. |
| 5,204,382 A | 4/1993 | Wallace et al. |
| 5,207,710 A | 5/1993 | Chu et al. |
| 5,211,661 A | 5/1993 | Shinjou et al. |
| 5,211,664 A | 5/1993 | Tepic et al. |
| 5,219,829 A | 6/1993 | Bauer et al. |
| 5,221,558 A | 6/1993 | Sonuparlak et al. |
| 5,236,458 A | 8/1993 | Ducheyne et al. |
| 5,236,786 A | 8/1993 | Newkirk et al. |
| 5,238,491 A | 8/1993 | Sugihara et al. |
| 5,256,292 A | 10/1993 | Cagle |
| 5,264,215 A | 11/1993 | Nakabayashi et al. |
| 5,276,068 A | 1/1994 | Waknine |
| 5,290,289 A | 3/1994 | Sanders et al. |
| 5,292,678 A | 3/1994 | Dhong et al. |
| 5,296,261 A | 3/1994 | Bouet et al. |
| 5,298,205 A | 3/1994 | Hayes et al. |
| 5,302,362 A | 4/1994 | Bedard |
| 5,306,307 A | 4/1994 | Senter et al. |
| 5,320,844 A | 6/1994 | Liu |
| 5,322,675 A | 6/1994 | Hakamatsuka et al. |
| 5,324,519 A | 6/1994 | Dunn et al. |
| 5,336,642 A | 8/1994 | Wolcott |
| 5,338,334 A | 8/1994 | Zhen et al. |
| 5,338,356 A | 8/1994 | Hirano et al. |
| 5,346,492 A | 9/1994 | Morgan |
| 5,352,715 A | 10/1994 | Wallace et al. |
| 5,409,982 A | 4/1995 | Imura et al. |
| 5,427,754 A | 6/1995 | Nagata et al. |
| 5,435,844 A | 7/1995 | Sasaya |
| 5,464,440 A | 11/1995 | Johansson |
| 5,496,399 A | 3/1996 | Ison et al. |
| 5,503,164 A | 4/1996 | Friedman |
| 5,522,893 A | 6/1996 | Chow et al. |
| 5,525,148 A | 6/1996 | Chow et al. |
| 5,531,794 A | 7/1996 | Takagi et al. |
| 5,545,254 A | 8/1996 | Chow et al. |
| 5,573,537 A | 11/1996 | Rogozinski |
| 5,573,771 A | 11/1996 | Geistlich et al. |
| 5,591,453 A | 1/1997 | Ducheyne et al. |
| 5,626,861 A | 5/1997 | Laurencin et al. |
| 5,645,934 A | 7/1997 | Marcolongo et al. |
| 5,660,778 A | 8/1997 | Ketcham et al. |
| 5,681,872 A | 10/1997 | Erbe |
| 5,702,449 A | 12/1997 | McKay |
| 5,707,962 A | 1/1998 | Chen et al. |
| 5,728,753 A | 3/1998 | Bonfield et al. |
| 5,755,792 A | 5/1998 | Brekke |
| 5,776,193 A | 7/1998 | Kwan et al. |
| 5,824,084 A | 10/1998 | Muschler |
| 5,834,008 A | 11/1998 | Greenspan et al. |
| 5,914,356 A | 6/1999 | Erbe |
| 5,928,243 A | 7/1999 | Guyer |
| 5,939,039 A | 8/1999 | Sapieszko et al. |
| 5,964,809 A | 10/1999 | Lin et al. |
| 5,977,204 A | 11/1999 | Boyan et al. |
| 5,984,968 A | 11/1999 | Park |
| 5,984,969 A | 11/1999 | Matthews et al. |
| 6,017,346 A | 1/2000 | Grotz |
| 6,019,765 A | 2/2000 | Thornhill et al. |
| 6,027,742 A | 2/2000 | Lee et al. |
| 6,049,026 A | 4/2000 | Muschler |
| 6,051,247 A | 4/2000 | Hench et al. |
| 6,077,989 A | 6/2000 | Kandel et al. |
| 6,180,605 B1 | 1/2001 | Chen et al. |
| 6,180,606 B1 | 1/2001 | Chen et al. |
| 6,187,047 B1 | 2/2001 | Kwan et al. |
| 6,190,643 B1 | 2/2001 | Stoor et al. |
| 6,214,368 B1 | 4/2001 | Lee et al. |
| 6,244,871 B1 | 6/2001 | Litkowski et al. |
| 6,287,341 B1 | 9/2001 | Lee et al. |
| 6,288,043 B1 | 9/2001 | Spiro et al. |
| 6,294,187 B1 | 9/2001 | Boyce et al. |
| 6,316,091 B1 | 11/2001 | Richart et al. |
| 6,325,987 B1 | 12/2001 | Sapieszko et al. |
| 6,328,765 B1 | 12/2001 | Hardwick et al. |
| 6,344,496 B1 | 2/2002 | Niederauer et al. |
| 6,383,159 B1 | 5/2002 | Saul et al. |
| 6,383,519 B1 | 5/2002 | Sapieszko et al. |
| 6,428,800 B2 | 8/2002 | Greenspan et al. |
| 6,458,162 B1 | 10/2002 | Koblish et al. |
| 6,482,427 B2 | 11/2002 | Yang |
| 6,521,246 B2 | 2/2003 | Sapieszko et al. |
| D473,648 S | 4/2003 | Muraca |
| 6,582,438 B2 | 6/2003 | DeMayo |
| 6,607,557 B1 | 8/2003 | Brosnahan et al. |
| 6,641,587 B2 | 11/2003 | Scribner et al. |
| 6,652,887 B1 | 11/2003 | Richelsoph et al. |
| 6,696,073 B2 | 2/2004 | Boyce et al. |
| 6,709,744 B1 | 3/2004 | Day et al. |
| 6,723,131 B2 | 4/2004 | Muschler |
| 6,863,899 B2 | 3/2005 | Koblish et al. |
| 6,881,766 B2 | 4/2005 | Hain |
| 6,949,251 B2 | 9/2005 | Dalal et al. |
| 6,969,501 B2 | 11/2005 | Sapieszko et al. |
| 6,987,136 B2 | 1/2006 | Erbe et al. |
| 6,991,803 B2 | 1/2006 | Sapieszko et al. |
| 7,045,125 B2 | 5/2006 | Erbe et al. |
| 7,156,880 B2 | 1/2007 | Evans et al. |
| 7,166,133 B2 | 1/2007 | Evans et al. |
| 7,189,263 B2 | 3/2007 | Erbe et al. |
| 7,235,107 B2 | 6/2007 | Evans et al. |
| 7,241,459 B2 | 7/2007 | Fechner et al. |
| 7,531,004 B2 | 5/2009 | Bagga et al. |
| 7,534,451 B2 | 5/2009 | Erbe et al. |
| 7,931,687 B2 | 4/2011 | Masuda et al. |
| 2002/0039552 A1 | 4/2002 | Sapieszko et al. |
| 2002/0062154 A1 | 5/2002 | Ayers |
| 2002/0127720 A1 | 9/2002 | Erbe et al. |
| 2003/0055512 A1* | 3/2003 | Genin et al. ............... 623/23.56 |
| 2003/0138473 A1 | 7/2003 | Koblish et al. |
| 2003/0193104 A1 | 10/2003 | Melican et al. |
| 2004/0127987 A1 | 7/2004 | Evans et al. |
| 2004/0138758 A1 | 7/2004 | Evans et al. |
| 2004/0254538 A1 | 12/2004 | Murphy et al. |
| 2005/0042288 A1 | 2/2005 | Koblish et al. |
| 2005/0169956 A1 | 8/2005 | Erbe et al. |
| 2005/0214340 A1 | 9/2005 | Erbe et al. |
| 2005/0288795 A1 | 12/2005 | Bagga et al. |
| 2006/0039951 A1 | 2/2006 | Sapieszko et al. |
| 2007/0066987 A1 | 3/2007 | Scanlan et al. |
| 2007/0122447 A1 | 5/2007 | Koblish et al. |
| 2007/0218098 A1 | 9/2007 | Reif et al. |
| 2008/0187571 A1 | 8/2008 | Clineff et al. |
| 2008/0221701 A1 | 9/2008 | Zhong et al. |
| 2008/0281431 A1 | 11/2008 | Missos |
| 2009/0068285 A1 | 3/2009 | LeGeros et al. |

FOREIGN PATENT DOCUMENTS

| | | |
|---|---|---|
| DE | 2208236 A1 | 9/1972 |
| EP | 0263489 A1 | 4/1988 |
| EP | 0417493 A2 | 3/1991 |
| EP | 1410811 A1 | 4/2004 |
| FR | 2664501 A1 | 1/1992 |
| GB | 2260538 A | 4/1993 |
| JP | 61201612 A | 9/1986 |
| JP | 62010939 A | 1/1987 |
| JP | 62067451 A | 3/1987 |
| JP | 62206445 A | 9/1987 |
| JP | 01167209 A | 6/1989 |
| JP | 01249059 | 10/1989 |
| JP | 02149408 A | 6/1990 |
| JP | 04208164 | 7/1992 |
| JP | 09048702 A | 2/1997 |
| JP | 09132406 A | 5/1997 |
| JP | 10243996 | 9/1998 |
| JP | 11106524 | 4/1999 |

| | | | |
|---|---|---|---|
| JP | 2001206787 A | 7/2001 | |
| JP | 2004136096 A | 5/2004 | |
| WO | 8706843 | 11/1987 | |
| WO | 9720521 A1 | 6/1997 | |
| WO | 9831630 A1 | 7/1998 | |
| WO | 9932163 | 7/1999 | |
| WO | 0042991 A1 | 7/2000 | |
| WO | 0045871 | 8/2000 | |
| WO | 0112106 | 2/2001 | |
| WO | 02058755 A2 | 8/2002 | |
| WO | 03053290 A1 | 7/2003 | |
| WO | 2004030655 | 4/2004 | |
| WO | 2004112855 A2 | 12/2004 | |
| WO | 2005009496 A1 | 2/2005 | |
| WO | 2005074614 A2 | 8/2005 | |
| WO | 2006031196 A1 | 3/2006 | |
| WO | 2007144662 A1 | 12/2007 | |
| WO | 2008002682 A2 | 1/2008 | |
| WO | 2010146312 A1 | 12/2010 | |

OTHER PUBLICATIONS

Ammann, "Strontium Ranelate: A Physiological Approach for an Improved Bone Quality," Bone, Sep. 2006, 38, pp. S15-S18.
Aras et al., "Trace Elements in Human Bone Determined by Neutron Activation Analysis", J. of Radioanalytical and Nuclear Chemistry, 1999, 239(1), 79-86.
Audran, "Drug Combination Strategies for Osteoporosis", Joint Bone Spine, May 6, 2006, 374-378.
Bachand, "Synthetic Osseous Grafting Materials: A Literature Review," http://das.cs.amedd.army.mil/journal/J9712.HTM, downloaded from internet on Mar. 4, 2005.
Barbara et al., "Normal Matrix Mineralization Induced by Strontium Ranelate in MC3T3-E1 Osteogenic Cells", Metabolism, Apr. 2004, 53(4), 532-537.
Bigi et al., "Isomorphous Substitutions in b-Tricalcium Phosphate: The Different Effects of Zinc and Strontium", J. of InorQanic Biochemistry, Jun. 1997, 66, 259-265.
Bigi et al., "Strontium-Substituted Hydroxyapatite Nanocrystals", Inorganic Chimica Acta, Feb. 2007, 360(3), 1009-1016.
Brown et al., "Variations in Solution Chemistry During the Low-Temperature Formation of Hydroxyapaptite," J. Am. Ceram. Soc., 1991, 74(8), pp. 1845-1854.
Brown, "Solubilities of Phosphate and Other Sparingly Soluble Compounds," Environmental Phosphorous Handbook, Chapter 10, 1973, pp. 203-289.
Canalis et al., "The Divalent Strontium Salt S12911 Enhances Bone Cell Replication and Bone Formation in Vitro", Bone, Jun. 1996, 18(6), 517-523.
Carroll et al., "The Trouble With Tocars; Barely Conscious," Smart Money, 2001.
Chaair et al., "Precipitation of stoichiometric apatitic tricalcium phosphate prepared by a continuous process," J. Mater. Chem., 1995, 5(6), pp. 895-899.
Cheung et al., "Vertebroplasty by use of a Strontium-Containing Bioactive Bone Cement", Spine, Sep. 1, 2005, 30(175), 584-591.
Clineff et al., "Analytical Technique for Quantification of Selected Resorbable Calcium Phosphate Bone Void Fillers with the Use of Polarized-light Microscopy", J Biomed Mater Res B Appl Biomater, Jan. 15, 2005, 72(1), 125-130.
Cornell et al., "Multicenter Trial of Collagraft as Bone Graft Substitute," J. of Orthopaedic Trauma, 1991, 5(1), pp. 1-8.
Dahl et al., "Incorporation and Distribution of Strontium in Bone", Bone, Apr. 2001, 28(4), 446-453.
Database EPODOC, European Patent Office, The Hague, NL; XP002676998, Jul. 31, 2001.
Database WPI Week 200172, Thomson Scientific, London, GB; AN 2001-620274, XP002676997, Jul. 31, 2001.
Driessens et al., "Effective forumulations for the preparation of calcium phosphate bone cements," J. Mat. Sci. Mat. Med., 1994, 5, pp. 164-170.
Driessens, F.C.M. et al., "Effective formulations for the preparation of calcium phosphate bone cements," J. Mat. Sci.: Mat. Med., 1994, 5, 164-170.

Elgayar, "The Influence of Alkali Metal Content and Network Connectivity on Bioactive Glasses", Thesis Submitted to University of London, May 2004, 152 pages.
Erbe et al., "Potential of an ultraporous B-tricalcium phosphate synthetic cancellous bone void filler and bone marrow aspirate composite graft", Eur. Spine J., Jun. 13, 2001, 10:S141-S146.
European Search Report and European Opinion for Application No. EP12151422 dated Jun. 11, 2012.
Famery et al., "Preparation of a- and b-Tricalcium Phosphate Ceramics, with and Without Magnesium Addition," Ceram. Int., 1994, 20, pp. 327-336.
Fowler, "Infrared Studies of Apatites. I. Vibrational Assigments for Calcium, Strontium, and Barium Hydroxyapatites Utilizing Isoptic Substition", Inorganic Chemistry, 1974, 13(1), 194-207.
Fowler, "Infrared Studies of Apatites. II. Preparation of Normal and Isotopically Substituted Calcium, Strontium, and Barium Hydroxyapatites and Spectra-Structure-Composition Correlations", Inorganic Chemistry, 1974, 13(1), 207-214.
Fukase et al., "Setting Reactions and Compressive Strengths of Calcium Phosphate Cements," J. Dent. Res., 1990, 69(12), pp. 1852-1856.
G.H. Nancollas In vitro studies of calcium phosphate crystallization Biomineralization—Chemical and Biochemical Perspectives 157-187 1989.
G.H. Nancollas The involvement of calcium phosphates in biological mineralization and dimeralization processes Pure Appl. Chem. 1992 64(11):1673.
Gentleman et al., "The Effects of Strontium-Substituted Bioactive Glasses on Osteoblasts and Osteoclasest in Vitro", Biomaterials, Feb. 2010, 31, 3949-3956.
Gorustovich et al., "Microchemical Characterization of Bone Around Strontium-Doped Bioactive Glass Particles", Abstracts, Bone, Oct. 2007, 41, S3.
Gorustovich et al., "Osteoconductivity of Strontium-Doped Bioactive Glass Particles", Abstracts, Bone, Dec. 2007, 41 (6), S4.
Gosain, "Bioactive Glass for Bone Replacement in Craniomaxillofacial Reconstruction," Bioactive Glass, 2004, 114 (2), pp. 590-593.
Greenwood et al., "Oxoacides of phosphorus and their salts," in Chemistry of the Elements, Pergamon Press, 1984, pp. 586-595.
Guo et al., "Development of a Strontium-Containing Hydroxyapatite Bone Cement", Biomaterials, Jun. 2005, 26(19), 4073-4083.
H. Chaair et al. Precipitation of stoichiometric apatitic tricalcium phosphate prepared by a continuous process J. Mater. Chem. 1995 5(6):895.
H. Monma et al. Properties of hydroxyapatite prepared by the hydrolysis of triacalcium phosphate J. Chem. Tech. Biotechnol. 1981 31:15.
Hanifi et al., "Effect of Strontium Ions Substitution on Gene Delivery Related Properties of Calcium Phosphate Nanoparticles", J. Mater. Sci. Mater. Med., Jul. 10, 2010, 21, 2601-2609.
Hench et al., "Biological Applications of Bioactive Glasses," Life Chemistry Reports, 1996, 13, pp. 187-241.
Holtorf, H. et al., Ectopic bone formation in rat marrow stromal cell/titanium fiber mesh scaffold constructs: Effect of initial cell photype, Biomaterials 26 (2005) pp. 6208-6216.
International Patent Application No. PCT/US201 0/061239: International Search Report dated May 2, 2011, 2 pages.
International Search Report dated Dec. 18, 2003 in PCT/US03/31370.
International Search Report, PCT/US2007/015424, dated Feb. 16, 2009.
Ishikawa et al., "Properties and mechanisms of fast-setting calcium phosphate cements," J. Mat. Sci. Mat. Med., 1995, 6, pp. 528-533.
Johal et al., "In Vivo Response of Strontium and Zinc-Based Ionomeric Cement Implants in Bone", J. of Materials Science: Materials in Medicine, Apr. 2002, 13(4), 375-379.
Jones, "Teeth and Bones: Applications of Surface Science to Dental Materials and Related Biomaterials", Surface Science Reoprts, May 2001, 42(3-5), 75-205.

Kim et al., "Strontium substituted calcium phosphate biphasic ceramics obtained by a powder precipitation method," Journal of Material Science: Materials in Medicine, Dec. 7, 2004, 15, pp. 1129-1134.

Kingery, Introduction to Chemistry, Wiley Series on the Science and Technology of Materials, 1st ed., Hollowman, J.H. et al. (eds.), Wiley & Sons, 1960, p. 416.

Kokubo and Takadama, How useful is SBF in predicting in vivo bone bioactivity?. Biomaterials (2006) 27: 2907-2915.

Koutsoukos et al., "Crystallization of Calcium Phosphates. A Constant Composition Study," J. Am. Chem. Soc., 1980, 102, 1553-1557.

Lacout, "Calcium Phosphate As Bioceramics," in Biomaterials—Hard Tissue Repair and Replacement, Elsevier Science Publishers, 1992, pp. 81-95.

Lam et al., "Solvothermal Synthesis of Strontium Phosphate Chloride Nanowire," J. of Crystal Growth, May 1, 2007, 306, pp. 129-134.

Landi et al., "Sr-Substituted Hydroxyapatites for Osteoporotic Bone Replacement", Acta Biomaterials, Jun. 2007, 3, 961-969.

Lee et al., "Tissue-engineered growth of bone by marrow cell transplantation using porous calcium metaphosphate matrices," G. Biomed. Mat. Res., 2001, 54(2), pp. 216-223.

Lee, Y-M., et al., "Tissue-engineered growth of bone by marrow cell transplantation using porous calcium metaphosphate matrices", G. Biomed. Mat. Research, 2001, 54(2), 216-223.

LeGeros, "Biodegradation and Bioresorption of Calcium Phosphate Ceramics," Clin. Mat., 1993, 14(1), pp. 65-88.

LeGeros, "Calcium Phosphates in Oral Biology and Medicine," Monographs in Oral Science, Meyers, H.M. (ed.), Karger Press, 1991, 15, pp. 108-129.

LeGeros, "Preparation and Octacalcium Phosphate (OCP): A Direction Fast Method," Calcif. Tiss. Int., 1985, 37, 194-197.

LeGeros, "Properties of Osteoconductive Biomaterials: Calcium Phosphate", Clinical Orthopaedics and Related Research, Feb. 2002, 395, 81-98.

LeGeros, R.Z., "Biodegradation and bioresorption of calcium phospate ceramics," Clin. Mat., 1993, 14(1), 65-88.

Li et al., "A Novel Injectable Bioactive Bone Cement for Spinal Surgery: A Developmental and Preclinical Study", J. Biomed Mater Res., Mar. 2000, 52, 164-170.

Li et al., "Characteristics and Mechanical Properties of Acrylolpamidronate Treated Strontium Containing Bioactive Bone Cement", Journal of Biomechanics, Poster Sessions, Jul. 4, 2007, 40(S2), S487.

Li et al., "Chemical Composition, Crystal Size and Lattice Structural Changes After Incorporation of Strontium into Biomimetic Apatite", Biomaterials, Mar. 2007, 28(7), 1452-1460.

Lickorish, David, et al. Collagen-hydroxyapatite composite prepared by biomimetic process, Journal of Biomedical Materials Research Part A. vol. 68A (Nov. 14, 2003), pp. 19-27.

Ling et al., "Expression of TGF-Beta in Region of Bone Defect Repaired by Collagent/Nano-Beta-Tricalcium Phosphate Composite Artificial Bone," Dabase Medline [online] US National Library of Medicine (NLM), Bethesda, MD, 2003, XP002537216, Database Accession No. NLM14526442, Abstract.

Llinas et al., "Structural Studies in Human Alkaline Phosphate in Complex with Strontium: Implication for It's Secondary Effect in Bones", Protein Science, Apr. 2006, 15, 1691-700.

Marie et al., "Mechanisms of Action and Therapeutic Potential of Strontium in Bone", Calcified Tissue International, Aug. 2001, 9, 121-129.

Marie, "Strontium Ranelate: New Insights into It's Dual Mode of Action", Bone, May 2007, 40(5/Supplement), S5-S8.

Matsumura et al., "Radiopacity and Physical Properties of Titanium-polymethacrylate Composite," J. of Dental Res., 1992, 71(1), pp. 2-6.

Mirtchi et al., "Calcium phosphate cements: Effect of fluorides on the setting and hardening of b-tricalcium phosphate-dicalcium phosphate-calcite cements," Biomat., 1991, 12, pp. 505-510.

Mirtchi et al., "Calcium phosphate cements: Effect of fluorides on the setting and hardening of beta-tricalcium phosphate-dicalcium phosphate-calcite cements," Biomat., 1991, 12, pp. 505-510.

Monma et al., "Properties of Hydroxyapatite Prepared by the Hydrolysis of Tricalcium Phosphate," J. Chem. Tech. Biotechnol., 1981, 31, pp. 15-24.

Nancollas et al., "Formation and Dissolution Mechanisms of Calcium Phosphates in Aqueous Systems," in Hydroxyapatite and Related Materials, CRC Press, Inc., 1994, pp. 73-81.

Nancollas, "In vitro studies of calcium phosphate crystallization," in Biomineralization Chemical and Biochemical Perspectives, 1989, pp. 157-187.

Nancollas, "The involvement of calcium phosphates in biological minerlization and demineralization processes," Pure Appl. Chem., 1992, 64(11), pp. 1673-1678.

Ni et al., "Interfacial Behaviour of Strontium-Containing Hydroxyapatite Cement with Cancellous and Cortical Bone", Biomaterials, Jun. 2006, 27, 5127-5133.

Ni et al., "Nano-Mechanics of Bone and Bioactive Bone Cement Interfaces in a Load-Bearing Model," Biomaterials, Mar. 2006, 27(9), pp. 1963-1970.

Ni et al., "Strontium-Containing Hydroxyapatite Bioactive Bone Cement in Revision Hip Arthroplasty", Biomaterials, May 2006, 27, 4348-4355.

Nielsen, "The Biological Role of Strontium", Bone, Jul. 2004, 35, 583-588.

Okayama et al., "The Mechanical Properties and Solubility of Strontium-Substituted Hydroxyapatite", Bio-Medical Materials and Engineering, 1991, 1 (1 ), 11-17.

Oliveira et al., "Strontium-Substituted Apatite Coating Grown on Ti6A14V Substrate Through Biomimetic Synthesis", J. Biomedical Materials Research Part B: Applied Biomaterials, Apr. 2007, 83B, 258-265.

Oonishi et al., "Particulate Bioglass Compared With Hydroxyapatite as a Bone Graft Substitute," Clinical Orthopaedics and Related Research, No. 334, pp. 316-325, Jan. 1997.

Ortolani and Vai, "Strontium Ranelate: An Increased Bone Quality Leading to Vertebral Antifracture Efficacy at All Stages," Bone, Feb. 2006, 38(2 Suppl 1), pp. S19-S22.

P.W. Brown et al. Variations in solution chemistry during the low temperature formation of hydroxyapatite J. Am. Ceram. Soc. 1991 74(8):1848.

PCT International Search Report dated Apr. 10, 1998, 1 page.

Pi and Quarles, "A Novel Cation-Sensing Mechanism in Osteoblasts is a Molecular Target", Journal of Bone and Mineral Research, Jan. 12, 2004, 19(5), 862-869.

Piotrowski et al., Mechanical studies of the bone bioglass interfacial bond. J. Biomed. Mater. Res. (1975) 9:47-61.

Powell et al., "The Structure of Ceramic Foams Prepared from Polyurethane-Ceramic Suspension," Materials & Manuf. Processes, 1995, 10(4), pp. 757-771.

Qiu et al, "Effect of strontium ions on the growth of ROS17/2.8 cells on porous calcium polyphosphate scaffolds," Biomaterials 27 (2006) pp. 1277-1286.

Robson, Wound Infection: a failure of wound healing caused by an imbalance of bacteria. (1997) Surg Clin North Am. pp. 637-650.

Satyanarayana et al., "One Dimensional Nanostructured Materials", Progress in Materials Science, Jul. 2007, 52(5), 699-913.

Stanley et al., Residual alveolar ridge maintenance with a new endosseous plant material. Journal of Prosthetic Dentistry, vol. 58, pp. 607-613 (1987).

Stoor P, Soderling E, Salonen JI. Antibacterial effects of a bioactive glass paste on oral microorganisms. Acta Odontol Scand 1998; 56(3):161-165.

Suh et al., "Delivery of Recombinant Human Bone Morphogenetic Protein-2 Using a Compression-Resistant Matrix in Posterolateral Spine Fusion in the Rabbit and in the Non-Human Primate," Database Medline [Online] US National Library of Medicine (NLM), Bethesda, MD, XP002537215, Database Accession No. NLM11840099, Abstract, Feb. 15, 2002.

Tampieri et al., Posority-graded hydroxyapatite ceramics to replace natural bone, Biomaterial, 2001, vol. 22, pp. 1365-1370.

The Independent Research Group, Jan. 28, 2003, pp. 1-41.

Tomisaka, "510(k) Summary; Origen™ DMB with bioactive glass," Nanotherapeutics, 2007, pp. 5-1 through 5-3; letter 3 pages.

U.S. Appl. No. 08/784,439, filed Jan. 16, 1997 Sapieszko et al.

U.S. Appl. No. 09/253,556, Sapieszko et al., filed Feb. 19, 1999.

Vaccaro, "The Role of Osteocondutive Scaffold in Synthetic Bone Graft", Orthopedics, May 2002, 25(5/Supplement), 1-8.

Verberckmoes et al., "Effects of Strontium on the Physicochemical Characteristics of Hydroxyapatite", Calcified Tissue International, Jul. 2004, 75, 405-415.

Vereecke et al., "Calculation of the Solubility Diagrams in the System $Ca(OH)_2$—$H_3PO_4$—KOH—$HNO_3$—$CO_2$—$H_2O$," J. Cryst. Growth, 1990, 104, pp. 820-832.

Vicente et al., "Ultrastructural Study of the Osteointegration of Bioceramics (Whitlockite and Composite Beta-TCP + Collagen) in Rabbit Bone," Database Medline [Online] US National Library of Medicine (NLM), Bethesda, MD, XP002537217, Database Accession No. NLM8882364, Abstract, Mar. 1996.

Webster's II New College Dictionary; 1995; p. 819.

White et al., "Replamineform Porous Biomaterials for Hard Tissue Implant Applications", J. Biomed. Mater. Res. Symposium, 1975, No. 6, 23-27.

Wilson J, Pigott GH, Schoen FJ, Hench L 1. Toxicology and biocompatibility of bioglasses. J Biomed Mater Res 1981; 15:805-817.

Wong et al., "In vivo Cancellous Bone Remodeling on a Strontium-Containing Hydroxyapatite (Sr-HA) Bioactive Cement", J. Biomed Mater Res., May 2004, 68A, 513-521.

Wong et al., "Prediction of Preciptation and Transformation Behavior of Calcium Phosphate in Aqueous Media," in Hydroxyapatite and Related Mateirals, Brown, P.W., et al. (eds.), CRC Press, Inc., 1994, pp. 189-196.

Wong et al., "Ultrastructural Study of Mineralization of a Strontium-Containing Hydroxyapatite (Sr-HA) Cement in vivo", J. Biomed. Mater. Res., Apr. 2004, 70A, 428-435.

Wu et al., "The Effect of Strontium Incorporation into $CaSio_3$ Ceramics on their Physical and Biological Properties," Biomaterials, Apr. 2007, 28, 3171-3181.

Xue et al., "Osteoprecursor Cell Response to Strontium-Containing Hydroxyapatite Ceramics", J. Biomed. Mater. Res., Feb. 2006, 79A, 804-814.

Zhao et al., "Surface Treatment of Injectable Strontium-Coating Bioactive Bone Cement for Vertebroplasty", J. Biomed. Mater. Res. Part B, Appl. Biomater, Apr. 2004, 69B(1), 79-86.

* cited by examiner

FIG. 8
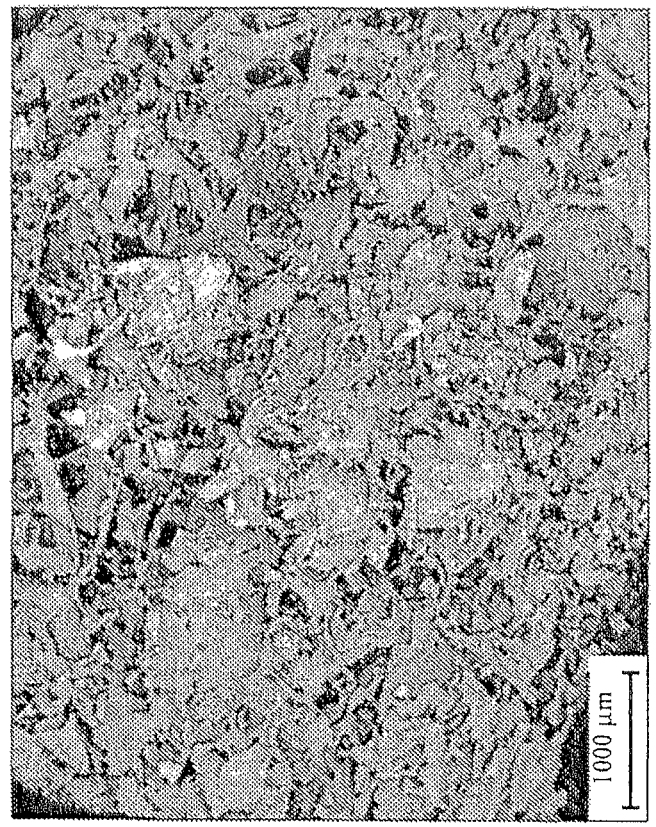
B
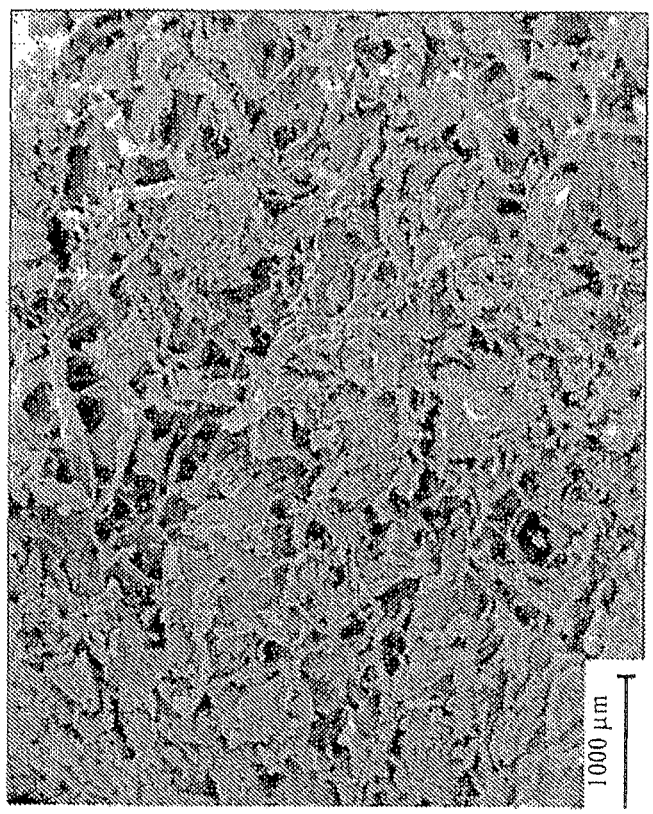
A

FIG. 9
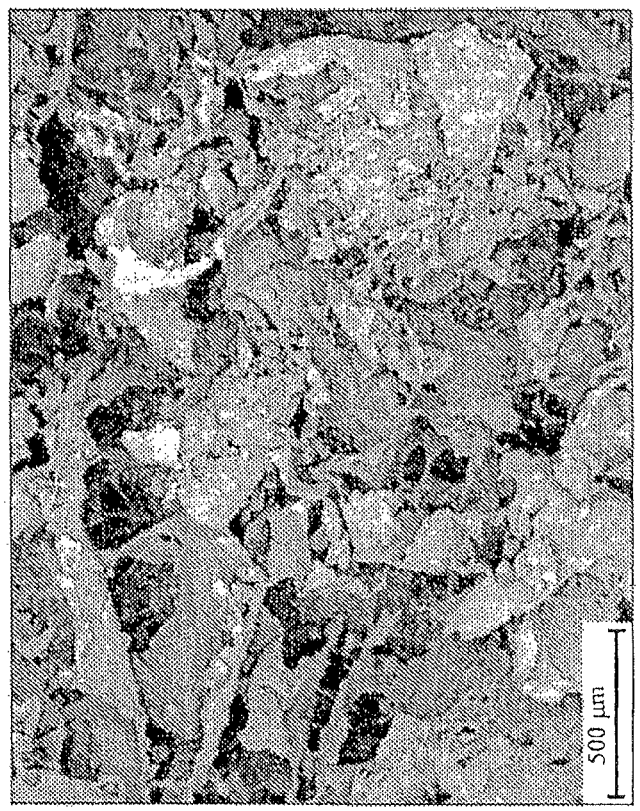
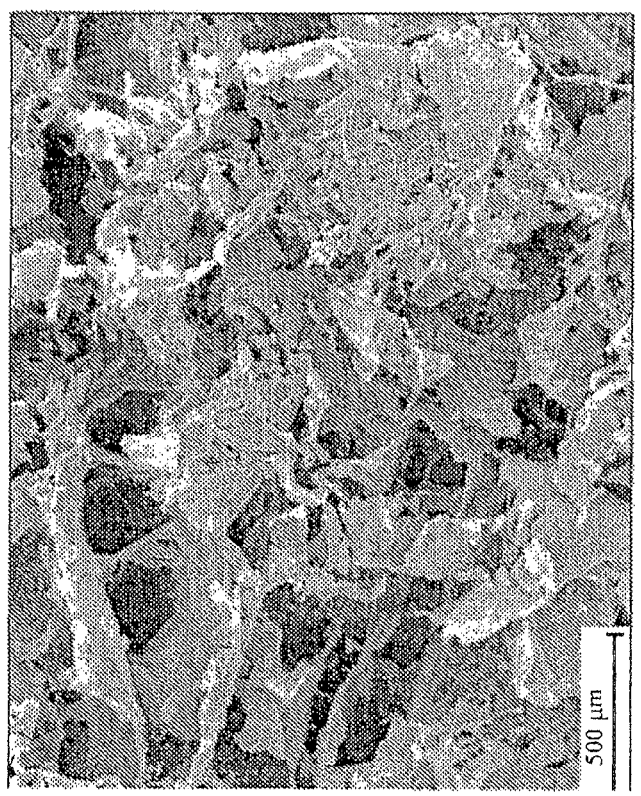

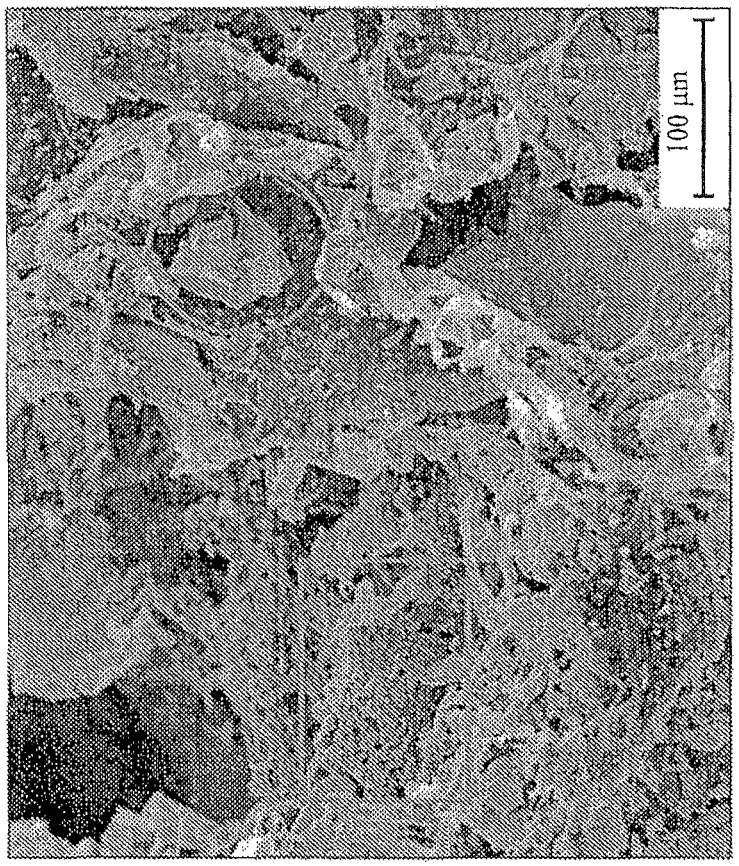
FIG. 12B 250x SE
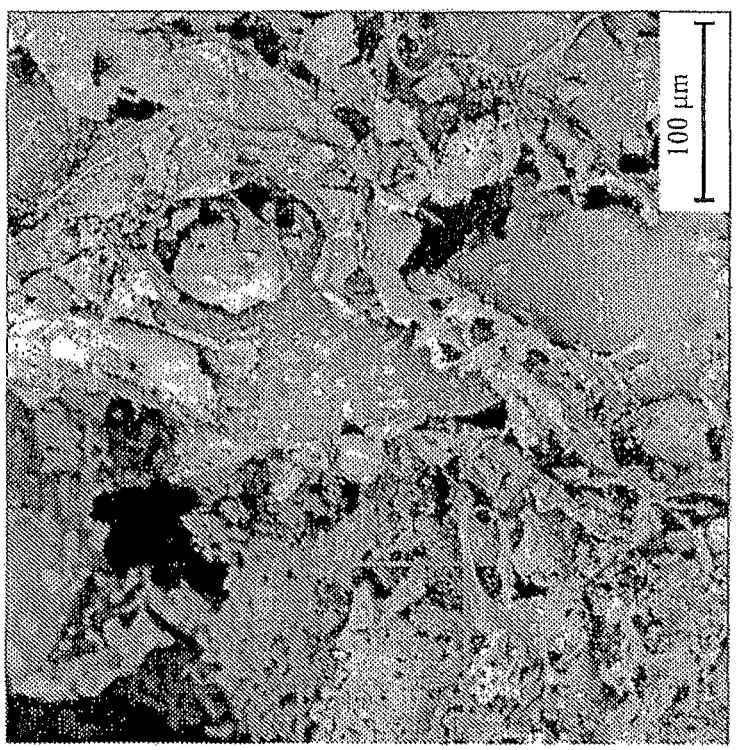
FIG. 12A 250x BSE

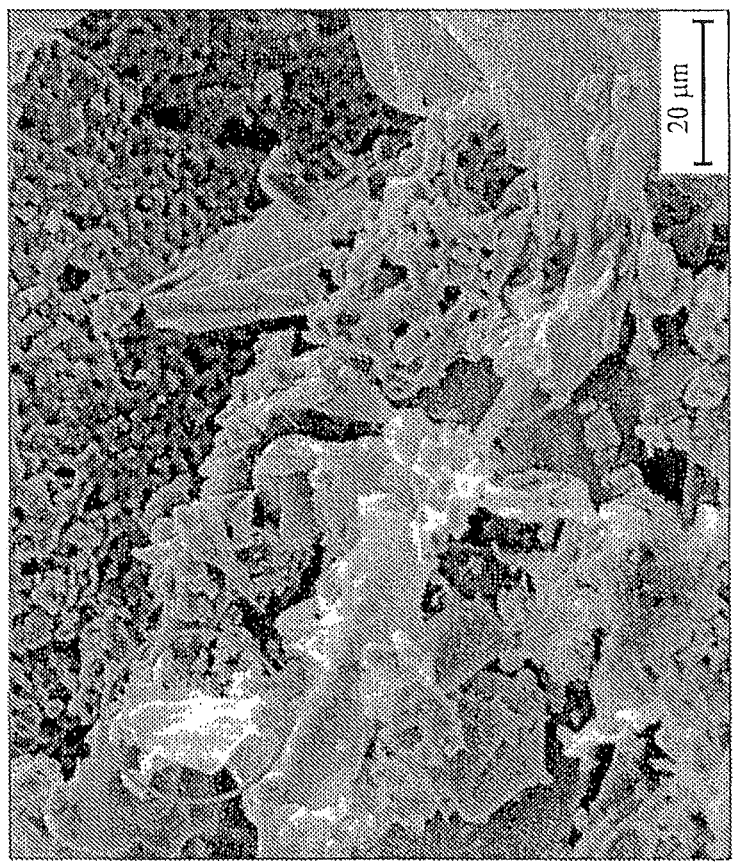
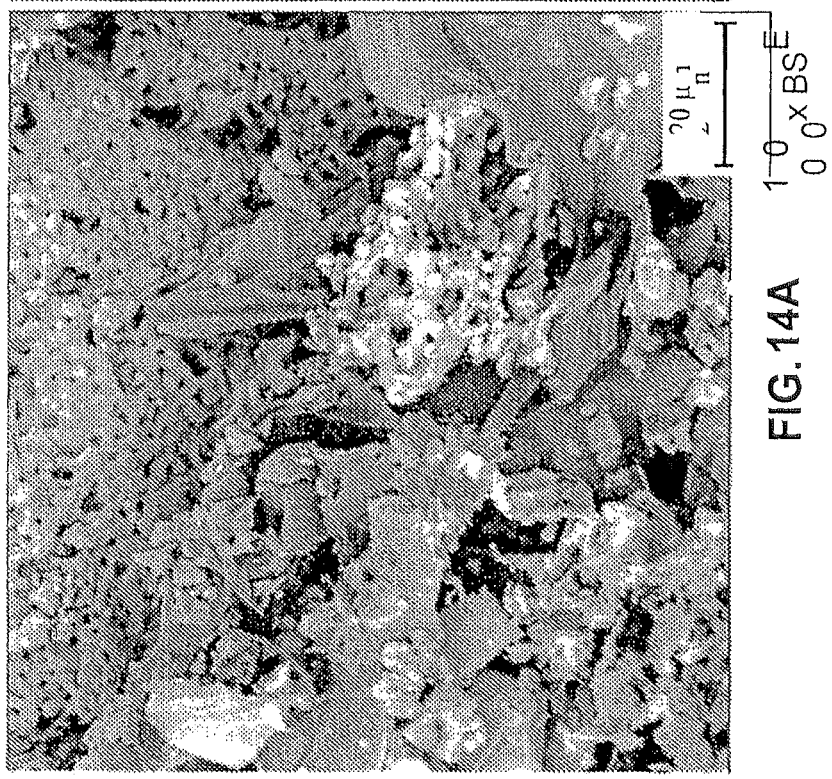
FIG. 14A
FIG. 14B

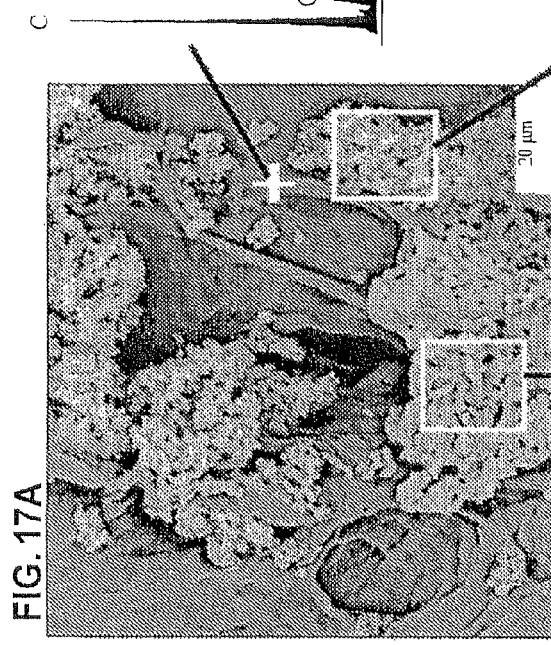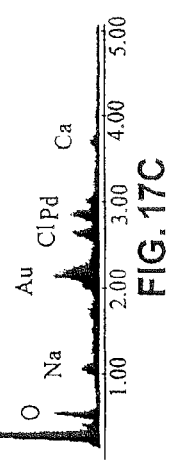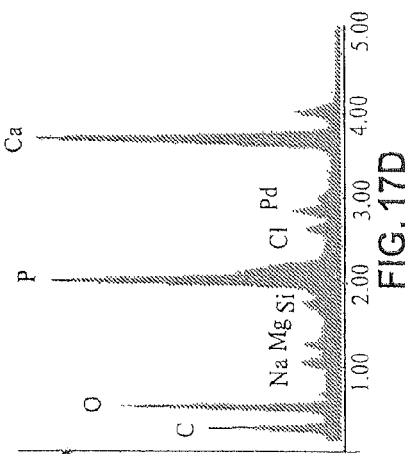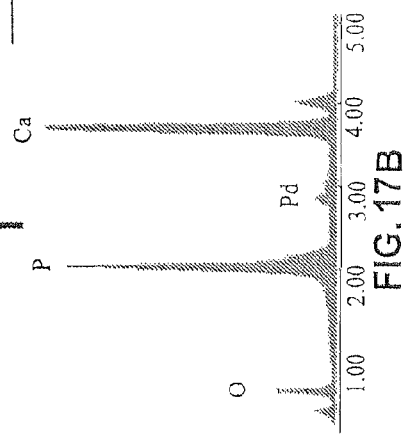

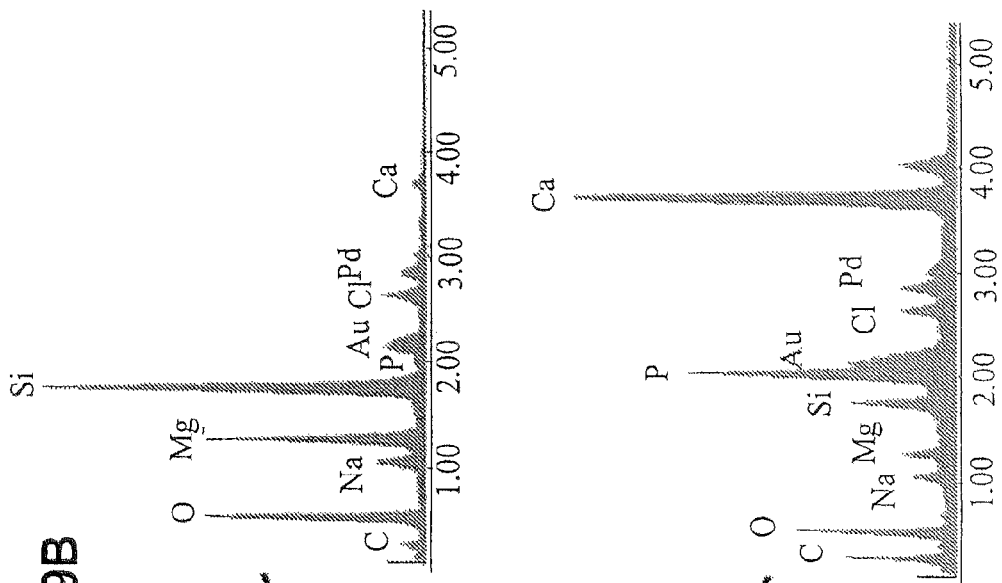
FIG. 19B
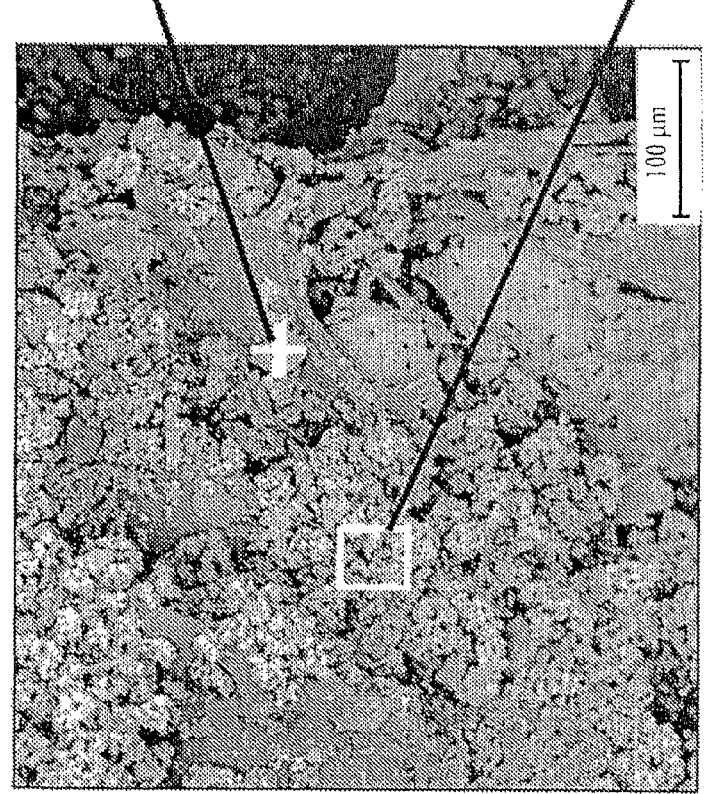
FIG. 19C
FIG. 19A

FIG. 20
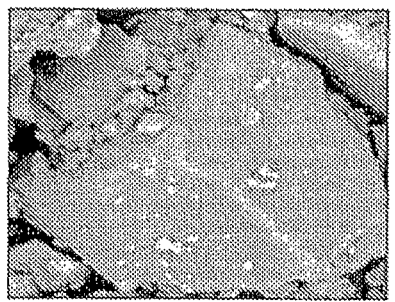
A Unreacted, 1000X magnification
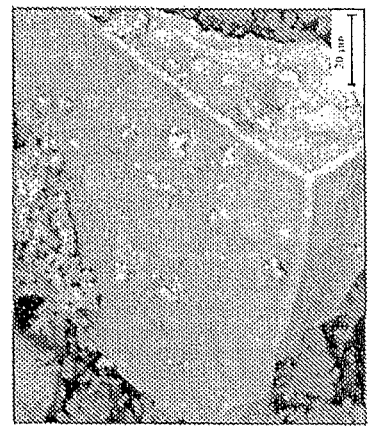
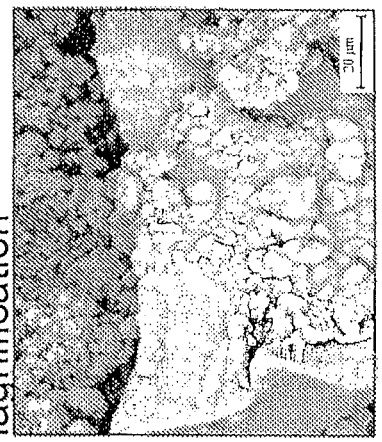
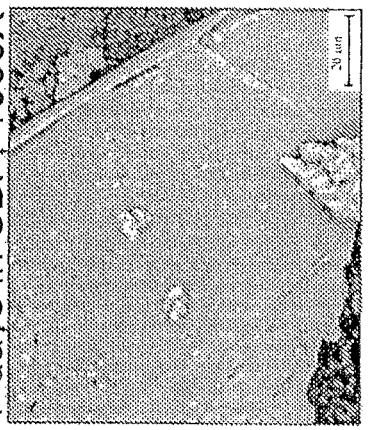
B 7 days in SBF, 1000X magnification Day 0, 100X Day 1, 2500X Day 7, 100X Day 14, 250X FIG. 25
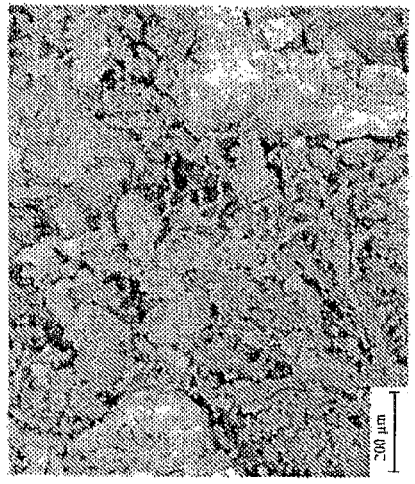
A 10% <53 μm combeite g-c, 100X
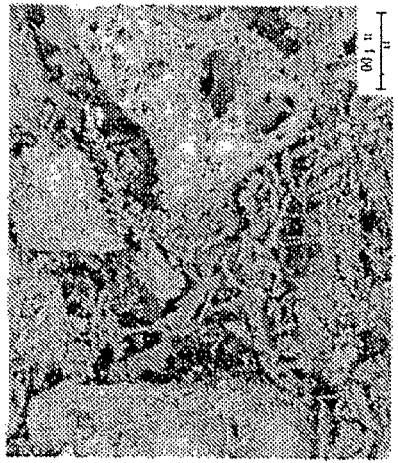
B 20% <53 μm combeite g-c, 100X
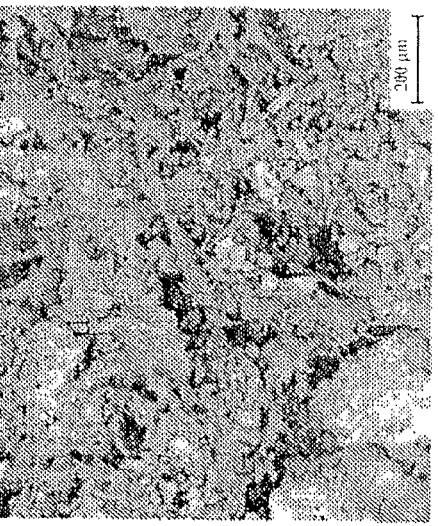
C 40% <53 μm combeite g-c, 100X FIG. 26
A 10% 38-250 μm bioactive glass, 100X
B 20% 38-250 mm bioactive glass, 100X
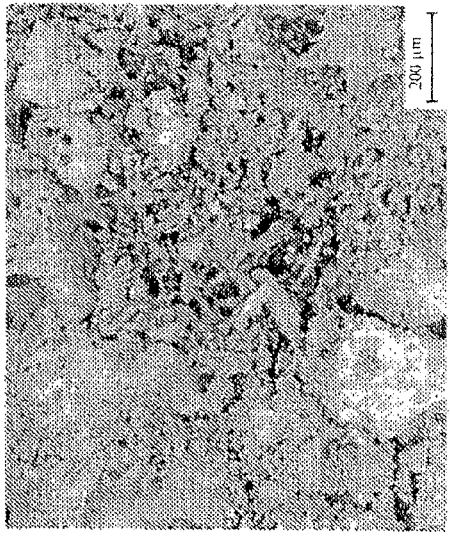
C 40% 38-250 mm bioactive glass, 100X FIG. 27
15% 90-150 μm combeite g-c, 100X
A
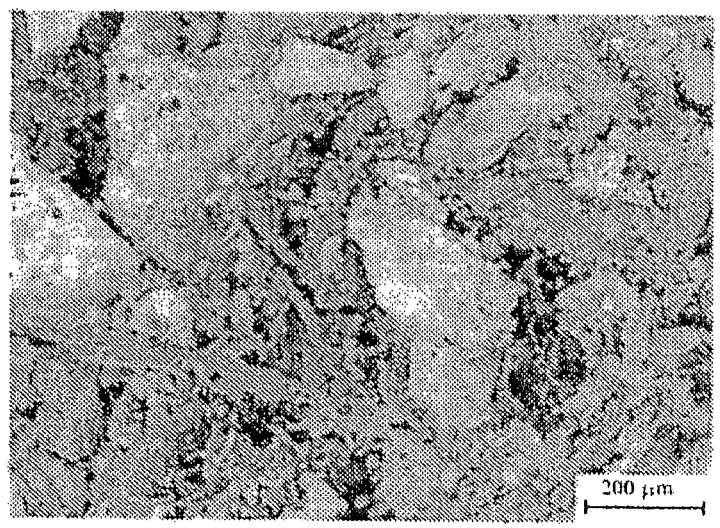
B
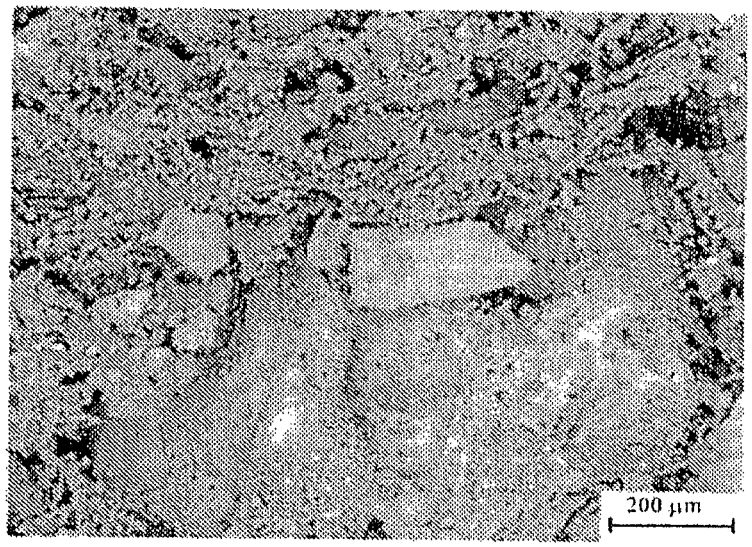

FIG. 29
A Unreacted
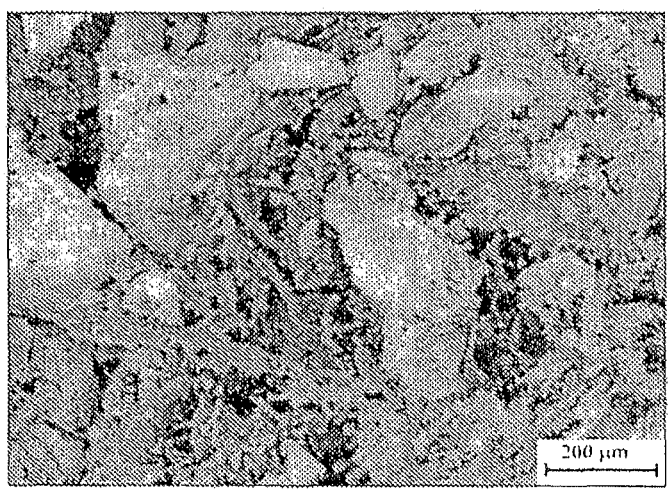
B 7 days in SBF
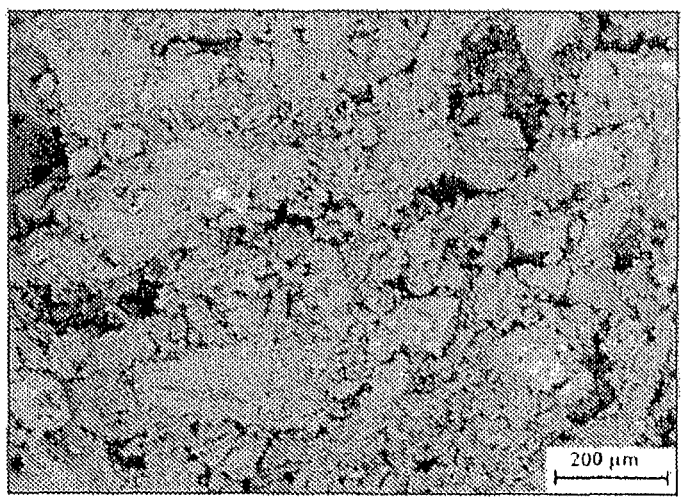

FIG. 30
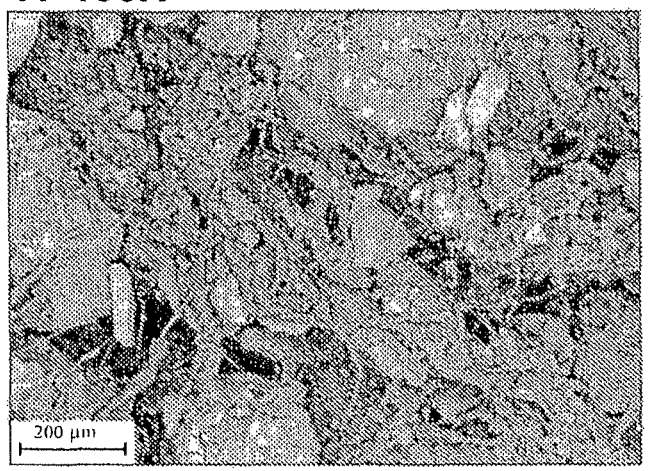
10% 90-150μm
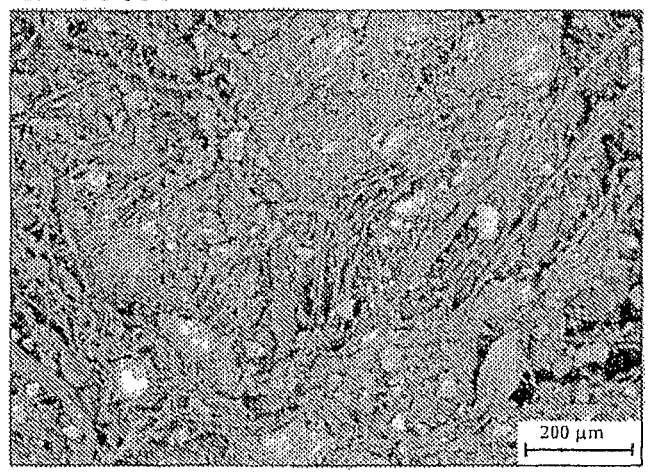
10% <53μm

FIG. 31
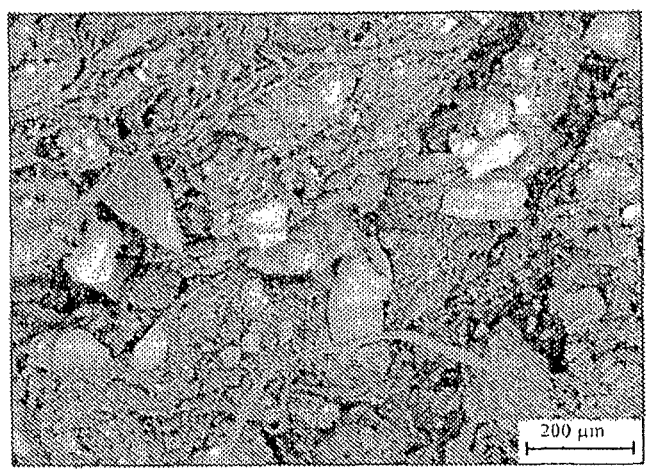
40% 90-150μm
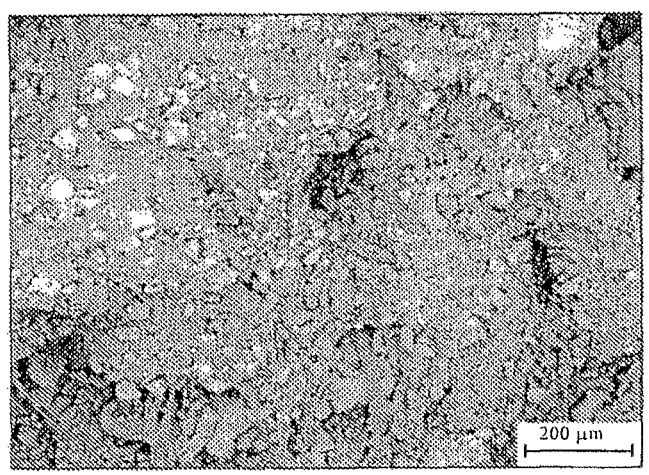
40% <53μm

BIOACTIVE BONE GRAFT SUBSTITUTE

CROSS-REFERENCE TO RELATED APPLICATIONS

The present application is a continuation of U.S. patent application Ser. No. 11/771,857, filed Jun. 29, 2007, now U.S. Pat. No. 8,303,967, which claims the benefit of filing date of U.S. Provisional Patent Application No. 60/817,617, filed Jun. 29, 2006, the disclosures of which are incorporated herein by reference.

FIELD OF THE INVENTION

This invention relates to biocompatible bone graft materials for repairing bone defects and the application of the bone graft materials disclosed herein. The present invention incorporates the benefits of inorganic shaped bodies having macro-, meso-, and microporosity, collagen, and bioactive glasses. The biocompatible bone graft materials of the present invention are also highly porous and homogeneous with interconnected macro-, meso-, and microporosity.

BACKGROUND OF THE INVENTION

There has been a continuing need for improved bone graft materials. Although autograft, the current "gold standard", has the ideal properties and radiopacity, the use of autogenous bone exposes the patient to a second surgery, pain, and morbidity at the donor site. Allograft devices, which are processed from donor bone, also carry the risk of disease transmission. The devices are restricted in terms of variations on shape and size and have sub-optimal strength properties that decrease after implantation. The quality of the allograft devices varies because the devices are natural. Also, since companies that provide allograft implants obtain their supply from donor tissue banks, there tend to be limitations on supply. In recent years, synthetic materials have become a viable alternative to autograft and allograft devices. One such synthetic material is Vitoss® Scaffold Synthetic Cancellous Bone Void Filler (Orthovita, Inc., Malvern, Pa., assignee of the present application). Synthetic graft materials, like autograft and allograft, serve as osteoconductive scaffolds that promote the ingrowth of bone. As bone growth is promoted and increases, the graft material resorbs and is eventually replaced with new bone.

Many synthetic bone grafts include materials that closely mimic mammalian bone, such as compositions containing calcium phosphates. Exemplary calcium phosphate compositions contain type-B carbonated hydroxyapatite [$Ca_5(PO_4)_{3x}(CO_3)_x(OH)$], which is the principal mineral phase found in the mammalian body. The ultimate composition, crystal size, morphology, and structure of the body portions formed from the hydroxyapatite are determined by variations in the protein and organic content. Calcium phosphate ceramics have been fabricated and implanted in mammals in various forms including, but not limited to, shaped bodies and cements. Different stoichiometric compositions such as hydroxyapatite (HAp), tricalcium phosphate (TCP), tetracalcium phosphate (TTCP), and other calcium phosphate salts and minerals, have all been employed to match the adaptability, biocompatibility, structure, and strength of natural bone. The role of pore size and porosity in promoting revascularization, healing, and remodeling of bone has been recognized as a critical property for bone grafting materials. The preparation of exemplary porous calcium phosphate materials that closely resemble bone have been disclosed, for instance, in U.S. Pat. Nos. 6,383,519 and 6,521,246, incorporated herein by reference in their entireties.

There has been a continued need for improved bone graft systems. Although calcium phosphate bone graft materials are widely accepted, many lack the strength, handling, and flexibility necessary to be used in a wide array of clinical applications. Heretofore, calcium phosphate bone graft substitutes have been used in predominantly non-load-bearing applications as simple bone void fillers and the like. For more clinically challenging applications that require the graft material to take on load, bone reconstruction systems that pair a bone graft material to traditional rigid fixation systems are used. For instance, MacroPore OS™ Reconstruction System is intended to reinforce and maintain the relative position of weak bony tissue such as bone graft substitutes or bone fragments from comminuted fractures. The system is a resorbable graft containment system composed of various sized porous sheets and sleeves, non-porous sheets and sleeves, and associated fixation screws and tacks made from polylactic acid (PLA). However, the sheets are limited in that they can only be shaped for the body when heated.

The Synthes SynMesh™ consists of flat, round, and oval shaped cylinders customized to fit the geometry of a patient's anatomical defect. The intended use is for reinforcement of weak bony tissue and is made of commercially pure titanium. Although this mesh may be load-bearing, it is not made entirely of resorbable materials that are flexible.

A number of different glasses, glass-ceramics, and crystalline phase materials have been used, either alone or in combination with acrylic polymerizable species, and other families of polymers, for restorative purposes. These include hydroxyapatite, fluorapatite, oxyapatite, Wollastonite, anorthite, calcium fluoride, agrellite, devitrite, canasite, phlogopite, monetite, brushite, octocalcium phosphate, Whitlockite, tetracalcium phosphate, cordierite, and Berlinite. Representative patents describing such uses include U.S. Pat. Nos. 3,981,736, 4,652,534, 4,643,982, 4,775,646, 5,236,458, 2,920,971, 5,336,642, and 2,920,971. Additional references include Japanese Patent No. 87-010939 and German Patent OS 2,208,236. Other references may be found in W. F. Brown, "Solubilities of Phosphate & Other Sparingly Soluble Compounds," Environmental Phosphorous Handbook, Ch. 10 (1973). All of the foregoing are incorporated herein by reference to provide disclosure, inter alia, of prior restorative materials and methods and compositions which may be included in the compositions and methods of the invention, as well as methods which may be employed as part of or ancillary to the invention.

There is a need for synthetic, resorbable bone grafts with improved handling, which are flexible and not brittle, and are compression resistant. There is also a need for flexible, compression-resistant bone grafts that are osteostimulative, osteoconductive, and osteoinductive.

There is also a need for resorbable bone grafts that are bioactive or osteoactive by nature of their ability to expediently form bone bonding.

There is a further need for resorbable bone grafts that are highly porous and have interconnected macro-, meso-, and microporosity for promoting capillary action of fluids, allowing recruitment of cells for bone formation, and permitting angiogenesis. There is also a need for bone grafts with fluid wicking and retention properties capable of delivering cells and molecules to the body There is a need for bioactive flowable or moldable, shapeable graft materials that can occupy voids of varying shapes for restoring defects in bone.

There is also a need for injectable, resorbable bone graft materials with improved handling properties.

SUMMARY OF THE INVENTION

The present invention relates to biocompatible bone graft materials comprising resorbable calcium phosphate, resorbable collagen, and bioactive glass. The invention also relates to biocompatible bone graft materials comprising calcium phosphate; biocompatible, resorbable collagen; and bioactive glass, wherein the graft has macro-, meso-, and microporosity. Also provided are composite biocompatible bone graft materials comprising a biocompatible, resorbable, substantially homogeneous blend of calcium phosphate having macro-, meso, and microporosity; biocompatible, resorbable collagen; and bioactive glass.

Also disclosed are methods for restoring or repairing bone in a mammal comprising accessing a bony space to be restored; and, placing into said bony space a bone graft material comprising calcium phosphate, biocompatible, resorbable collagen, and bioactive glass. There are also provided methods for restoring or repairing bone in a mammal comprising providing a bone graft material comprising calcium phosphate and biocompatible, resorbable collagen; wetting said bone graft material with a biologically compatible fluid; incorporating bioactive glass into said bone graft material; and, placing said bone graft into a bony space. Also provided are methods of modulating the rate of collagen resorption by adding a pH-altering material to a composition comprising collagen.

The present application also provides kits comprising a biocompatible bone graft comprising resorbable collagen and calcium phosphate; and, a quantity or container of bioactive glass.

BRIEF DESCRIPTION OF THE DRAWINGS

FIG. 8A is a SEM (secondary, 20×) of one embodiment of the bone graft material of the present invention, comprising 80% by weight of calcium phosphate, 10% collagen, and 10% combeite glass-ceramic. FIG. 8B is a SEM (backscatter, 20×) of one embodiment of the bone graft material of the present invention, comprising 80% by weight of calcium phosphate, 10% collagen, and 10% combeite glass-ceramic.

FIG. 9A is a SEM (secondary, 50×) of one embodiment of the bone graft material of the present invention, comprising 80% by weight of calcium phosphate, 10% collagen, and 10% combeite glass-ceramic. FIG. 9B is a SEM (backscatter, 50×) of one embodiment of the bone graft material of the present invention, comprising 80% by weight of calcium phosphate, 10% collagen, and 10% combeite glass-ceramic.

FIGS. 12A and 12B are SEMs (250×) of one embodiment of the present invention comprising 80% by weight of calcium phosphate, 10% collagen, and 10% combeite glass-ceramic. The porous structure of the calcium phosphate is identified by the boxed area. The combeite glass-ceramic particles are circled.

FIGS. 14A and 14B are SEMs (1000×) depicting the microstructure detail of one embodiment of the present invention, comprising 80% by weight of calcium phosphate, 10% collagen, and 10% combeite glass-ceramic. Areas of combeite glass-ceramic are circled.

FIGS. 15A and 15B are magnified 100×. FIG. 15C is magnified 250×.

FIG. 17A is a SEM (magnified 1000×) of one embodiment of the present invention, comprising 80% by weight of calcium phosphate, 15% collagen, and 5% combeite glass-ceramic, after immersion in SBF for four weeks. FIG. 17B is an EDAX spectra of an area of Vitoss® in FIG. 17A. FIG. 17C is an EDAX spectra of an area of collagen in FIG. 17A. FIG. 17D is an EDAX spectra of an area of new calcium phosphate growth in FIG. 17A based on a morphology distinct from that of the calcium phosphate.

FIGS. 18A and 18B are magnified 100×. FIG. 18C is magnified 250×.

FIG. 19A is a SEM (magnified 250×) of one embodiment of the present invention, comprising 80% by weight of calcium phosphate, 10% collagen, and 10% combeite glass-ceramic, after immersion in SBF for four weeks. FIG. 19B represents the EDAX spectra of an area of combeite glass-ceramic in FIG. 19A. FIG. 19C represents the EDAX spectra of the boxed area of FIG. 19A, representing new calcium phosphate growth on the bone graft substitute.

FIG. 20A is a SEM (1000× magnification) of a bioactive glass-ceramic in accordance with the invention. FIG. 20B is a SEM (1000× magnification) of a bioactive glass-ceramic in accordance with the invention showing calcium phosphate growth on the surface of the glass-ceramic.

FIG. 25 shows representative SEM images (100× magnification) of embodiments of the present invention containing 10, 20, or 40% by weight of combeite glass-ceramic having particle size of <53 μm.

FIG. 26 shows representative SEM images (100× magnification) of embodiments of the present invention containing 10, 20, or 40% by weight of 45S5 bioactive glass having particle size of 38-250 μm.

FIG. 27 shows representative SEM images (100× magnification) of embodiments of the present invention containing 15% by weight of combeite glass-ceramic having particle size of 90-150 μm.

FIG. 29A shows a representative SEM of a bone graft of one embodiment of the present invention comprising calcium phosphate, collagen, and bioactive glass. FIG. 29B shows a representative SEM of a bone graft after 7 days in SBF.

FIG. 30A shows a representative SEM (100× magnification) of an embodiment of a moldable bone graft to which 10% of combeite glass ceramic with particle size of 90-150 μm has been added. FIG. 30B shows a representative SEM (100× magnification) of an embodiment of a moldable bone graft to which 10% of combeite glass ceramic with particle size of <53 μm has been added.

FIG. 31A shows a representative SEM (100× magnification) of an embodiment of a moldable bone graft to which 40% of combeite glass ceramic with particle size of 90-150 μm has been added. FIG. 31B shows a representative SEM (100× magnification) of an embodiment of a moldable bone graft to which 40% of combeite glass ceramic with particle size of <53 μm has been added.

DETAILED DESCRIPTION OF ILLUSTRATIVE EMBODIMENTS

Figure 1:
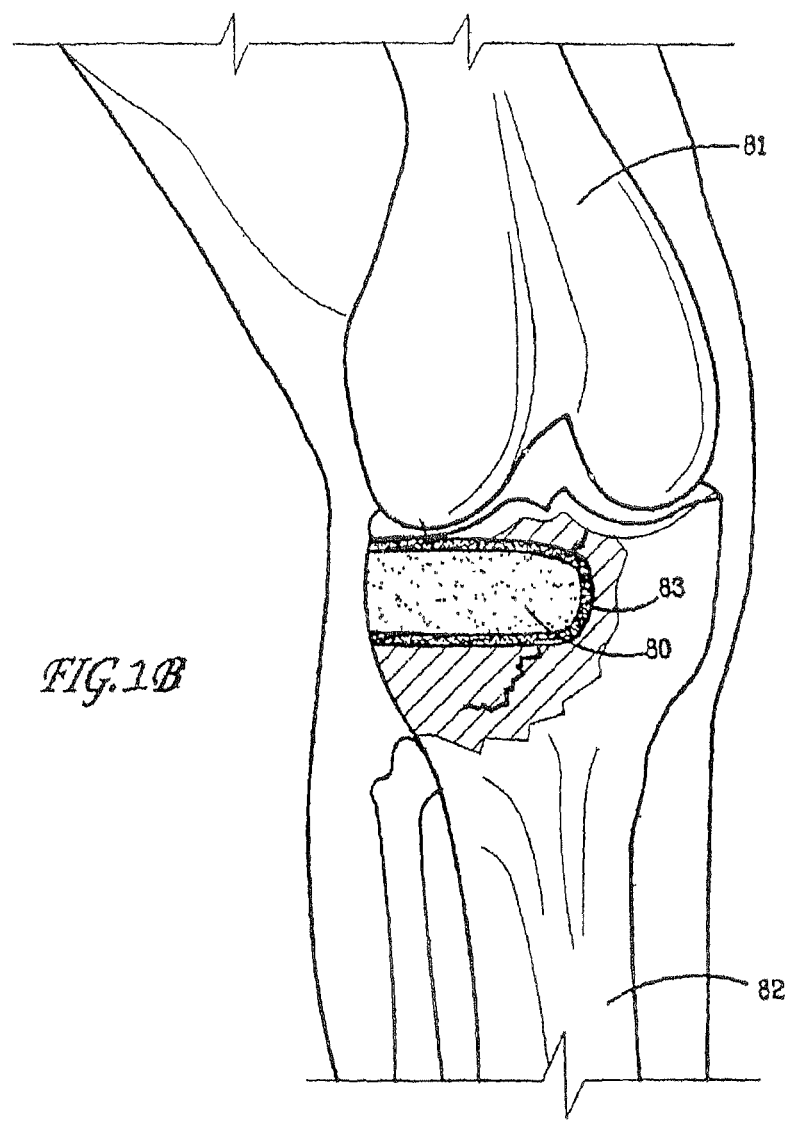
FIG. 1A illustrates one basic form of the biocompatible graft material in cylinder form.
FIG. 1B depicts the graft material in cylindrical form 80 inserted into a bone void 83 below the femur 81 in the tibial plateau 82 within a human knee.
Figure 2:
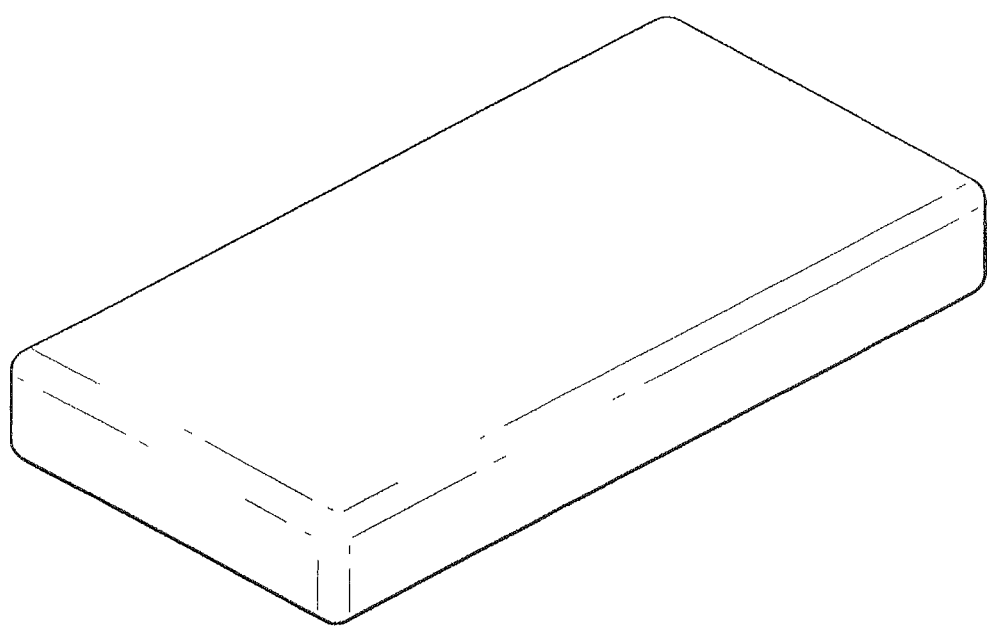
FIG. 2 illustrates another basic form of the present invention in strip form.

It has been discovered that admixing three constitutents: (1) highly porous resorbable inorganic material; (2) resorbable collagen; and (3) resorbable bioactive glass/glass-ceramic provides an osteostimulative and osteoconductive implant with improved resorption and bone formation properties, yet still provides a bone graft substitute with flexible, pliable, or flowable handling properties that allow the material to be manipulated, for example, wrapped, cut, bended, and/or shaped, particularly when wetted. Implants of the present invention provide an easy-to-use dose of composite material and provide an advancement over current bone reconstruction systems for certain clinical applications.

In accordance with the present invention, graft materials are provided comprising the oxidation-reduction reaction product of at least one metal cation, at least one oxidizing agent, and at least one oxidizable precursor anion; biocompatible, resorbable collagen; and a bioactive glass. Preferably, the reaction product is (synthetic) calcium phosphate having macro-, meso-, and microporosity. More preferably, the reaction product is β-tricalcium phosphate having macro-, meso-, and microporosity. More preferably, the porosity of the calcium phosphate is interconnected. The preparation of preferred forms of calcium phosphate for use in the present invention is described in U.S. Pat. Nos. 6,383,519 and 6,521,246, assigned to the assignee of the present invention and incorporated herein by references in their entireties. An exemplary calcium phosphate product is Vitoss® Scaffold Synthetic Cancellous Bone Void Filler (Orthovita, Inc., Malvern, Pa.). Porous calcium phosphate morsels are preferably greater than about 0.25 mm in size. The morsels of calcium phosphate may be about 1-2 mm in size for some embodiments of the present invention. The calcium phosphate morsels may be about 0.25 mm to about 1 mm or to about 2 mm for some embodiments of the present invention. For flowable compositions of the present invention, it will be appreciated that the morsel size will be selected considering the desired delivery apparatus. For example, for delivery of a flowable composition using a standard syringe, it will be necessary to select a morsel size that fits through the syringe orifice. Selection of the appropriate morsel size is believed to be with the capability of the skilled artisan.

Suitable collagens are described, for example, in U.S. Pat. No. 7,189,263, which is herein incorporated by reference in its entirety. Some embodiments of the present invention contain collagen that comprises up to 100% Type I collagen. In other embodiments, the collagens used may be predominantly, or up to about 90%, of Type I collagen with up to about 5% of Type III collagen or up to about 5% of other types of collagen. Suitable Type I collagens include native fibrous insoluble human, bovine, porcine, or synthetic collagen, soluble collagen, reconstituted collagen, or combinations thereof.

Bone graft materials of the present invention may be flexible or moldable, or the materials may be flowable. The nature of the collagen affects the flexibility, moldability, or flowability of the graft material. A graft containing predominantly fibrous collagen will be flexible or moldable upon wetting, depending on the degree of cross-linking of the collagen. A graft containing primarily soluble collagen with limited or no cross-links will be flowable upon wetting. Collagens suitable for use in the present invention include, but are not limited to, Semed F or Semed S (manufactured by Kensey Nash Corporation of Exton, Pa.), or combinations thereof.

"Bioactive glass" as used herein may be any alkali-containing ceramic, glass, glass-ceramic, or crystalline material that reacts as it comes in contact with physiologic fluids including, but not limited to, blood and serum, which leads to bone formation. In preferred embodiments, bioactive glasses, when placed in physiologic fluids, form an apatite layer on their surface. Examples of preferred bioactive glasses suitable for use in the present invention are described in U.S. Pat. No. 5,914,356, incorporated herein by reference. Suitable bioactive materials also include 45S5 glass and glass-ceramic, 58S5 glass, S53P4 glass, apatite-wollastonite containing glass and glass-ceramic. Preferably, the bioactive glass is a glass-ceramic composition comprising heterogeneous particles having an irregular morphology and regions of combeite crystallites ("combeite glass-ceramic"). In some embodiments, the bioactive glass comprises about 5-50% by volume of regions of combeite crystallites. Preferred bioactive glasses suitable for use in the present invention are those compositions comprising calcium-phosphorous-sodium-silicate and calcium-phosphorous-silicate. Such bioactive glasses include NovaBone® and NovaBone®-AR, distributed by NovaBone Products, LLC, Alachua, Fla. Further bioactive glass compositions that may be suitable for use in the present invention are described in U.S. Pat. No. 6,709,744.

While not wishing to be bound by theory, it is believed that resorption of bioactive glass particles of about 150 µm or less occurs as silica as released within the apatite gel layer, while larger particles are eventually broken down by osteoclasts (Goasin, A. Bioactive Glass for Bone Replacement in Craniomaxillofacial Reconstruction, Plastic and Reconstructive Surgery (2004) Vol. 114, No. 2, pp. 590-593). It is presently believed that the bone graft materials of the present invention provide an appropriate scaffold for bone growth independent of the bioactive glass. Again, while not wishing to be bound by theory, the role of the bioactive glass in bone grafts described herein is believed to be stimulatory to osteoblasts, and as such, large particles of glass (>150 µm) which may also provide a scaffold for bone growth are not necessary for the object of the invention to be served, and thus the particles which are resorbed via dissolution are preferred. However, all sizes of resorbable glass particles are contemplated as suitable.

Particle size measurement is well known in the art. Unless otherwise specified, particle size as used herein refers to the sieve size used to partition the glass particles. The bioactive glass particles used in accordance with the present invention are preferably about 90 to about 150 µm. The bioactive glass may be in the form of particles on the order of 1-2 mm. The bioactive glass particles may be on the order of about 100 µm or less, on the order of about 150 µm or less, or the bioactive glass particles can be on the order of about 50 to about 200 µm, about 75 to about 175 µm, or about 80 to about 160 µm.

Another suitable method of measuring particle size is via light scattering (for example by a light scattering particle size analyzer). In some embodiments of the present invention, the median particle size is about 2 to about 200 µm, as measured by light scattering. In other embodiments, the median particle size is about 2 to about 20 µm as measured by light scattering. In other embodiments, the median particle size is about 10 to about 20 µm as measured by light scattering. In other embodiments, the median particle size is about 100 to 200 µm as measured by light scattering.

The collagen and bioactive glass may be combined with the calcium phosphate by blending to form a substantially homogenous mixture. As used in this context, substantially homogenous means that the ratio of components within the mixture is the same throughout. The calcium phosphate, collagen, and bioactive glass may also be combined to form a composite matrix in various shapes and sizes. In certain embodiments, the bioactive glass could be in the form of a coating on the collagen strands. In others, the bioactive glass could be in the form of a coating on a collagen and calcium phosphate homogenous mixture. Upon treatment using various preferred heating, freeze-drying, and crosslinking techniques, such mixtures of the present invention form graft materials that may be preferred. In one method, the three constituents (the inorganic component, collagen, and bioactive glass), are mixed while the pH of the homogenate is monitored. The bioactive component is sensitive to aqueous environments, so monitoring the pH of the homogenate ensures that the bioactive glass component in the mix is not altered via premature leaching of ions that are necessary for promoting osteoactivity. The homogenate is then dispersed into defined molds, freeze-dried, and for some embodiments, crosslinked.

In another method, the collagen and the inorganic component are combined as described, and the bioactive glass is provided as a distinct component, to be incorporated into the bone graft material during preparation for use in the surgical site. Contemplated herein is a kit comprising a bone graft of the present invention and bioactive glass. The bone graft provided in a kit may comprise collagen and calcium phosphate. In a kit, the bioactive glass may be provided in a unit dose to be combined with the unit dose of bone graft provided. The bioactive glass may be provided in a container.

The bone graft provided in a kit may be enclosed in a delivery apparatus, such as a syringe, or, the bone graft may be provided in addition to a syringe capable of holding and delivering the bone graft. Flowable bone graft materials (such as those described in U.S. patent application Ser. No. 10/874,994, filed on Jun. 23, 2004, incorporated herein by reference in its entirety) are contemplated as being particularly suitable for such a kit. The bioactive glass may be within the delivery or holding apparatus along with the graft, or the bioactive glass may be provided in a second apparatus, such as a syringe. The bioactive-glass-containing apparatus may be adapted to connect to the bone graft apparatus such that homogenous mixing back and forth is permitted. Thus, ultimately, a composite apparatus capable of mixing the components into a substantially homogenous bone graft containing calcium phosphate, collagen, and bioactive glass is provided.

The admixture of the collagen and bioactive glass with the highly porous reaction product results in a graft that is highly porous with a broad pore size distribution, increased handling properties, and beyond that which is achievable with some forms of calcium phosphate alone. Moreover, grafts of the present invention exhibit improved osteoconductive and osteostimulatory properties over previous bone grafts. The resorption profile of some of the embodiments of the present invention may vary depending upon the amount, nature, and source of the collagen used. One reason that may explain the superior resorption properties of the present invention is the high degree of porosity retained even upon admixing the collagen and bioactive glass to form the reaction product. Bone grafts of the present invention are highly porous, highly porous being defined as having a total porosity of between about 65-95%.

Bone graft materials of this invention that may be preferred are held together in surgically relevant shapes and sizes by combining the reaction product with the collagen and the bioactive glass. It is also contemplated that the bioactive glass may be added as a layer or a coating on the surface of the surgically relevant shapes and sizes. The resulting articles retain substantially all of the biological and chemical properties of the shaped bodies taught in the '519 and '246 patents, while forming a shapeable, flexible unit dose. The bone graft materials may be manufactured into strips and cylinders of prescribed dimensions and volumes. The graft material will resorb following delivery in the surgical site and exhibit the same beneficial biological responses (e.g., bone formation) as the aforementioned shaped bodies.

In some embodiments, the bone graft materials of the present invention will comprise about 10-80% by weight of calcium phosphate; about 5-20% by weight of collagen; and about 5-80% by weight of bioactive glass. In other embodiments, the bone graft materials of the present invention will comprise about 50-90% by weight of calcium phosphate; about 5-25% by weight of collagen, and about 5-40% by weight of bioactive glass. In certain embodiments, bone graft materials of the present invention comprise calcium phosphate, collagen, and bioactive glass in a weight ratio of about 70:10:20. In other embodiments, the weight ratio of calcium phosphate, collagen, and bioactive glass is about 80:10:10. In yet others, the weight ratio of calcium phosphate, collagen, and bioactive glass is about 80:15:5. In further embodiments, the weight ratio of calcium phosphate, collagen, and bioactive glass is about 50:10:40. In others, the weight ratio of calcium phosphate, collagen, and bioactive glass is about 10:10:80. The weight ratio of the calcium phosphate, collagen, and bioactive glass may also be about 60:20:20. In a preferred embodiment, the weight ratio of the calcium phosphate, collagen, and bioactive glass is about 75:10:15. The mass ratios may be altered without unreasonable testing using methods readily available in the art while still maintaining all the properties (e.g., porosity, pore size distribution) that attribute to an effective bone graft (e.g., simultaneous bone formation, strength and graft resorption). One unique feature of the bone graft materials of the present invention is that the mineral remains porous even when combined with the collagen and bioactive glass. Further, the resultant bone graft is itself highly porous with a broad pore size distribution.

Preferably, bone graft materials of the present invention may comprise up to about 80% by weight of calcium phosphate. In certain embodiments, bone graft materials of the present invention may comprise up to about 70% by weight of calcium phosphate. The bone graft materials of the present invention may also comprise up to about 60% by weight of calcium phosphate. In other embodiments, bone graft materials of the present invention may comprise up to about 50% by weight of calcium phosphate. In yet others, the bone graft materials may comprise up to about 10% by weight of calcium phosphate. In some embodiments, the calcium phosphate is β-tricalcium phosphate. In some embodiments, the calcium phosphate has micro-, meso-, and macroporosity.

In certain variants of the present invention, the bone graft materials may comprise up to about 5% by weight of collagen. In certain other variants of the present invention, the bone graft materials may comprise up to about 15% by weight of collagen. In other variants, the bone graft materials may comprise up to about 10% by weight of collagen. In yet others, the bone graft materials may comprise up to about 20% by weight of collagen.

Bone graft materials of the present invention may comprise up to about 40% by weight of bioactive glass. The bone graft materials of the present invention may comprise up to about 20% by weight of bioactive glass. In certain embodiments, bone graft materials of the present invention may comprise up to about 15% by weight of bioactive glass. In certain other embodiments, bone graft materials of the present invention may comprise up to about 10% by weight of bioactive glass. In other embodiments, bone graft materials of the present invention may comprise up to about 5% by weight of bioactive glass. It is envisioned that in some embodiments, the bone graft materials may comprise up to about 80% of bioactive glass. In some embodiments, the bone graft material is provided in a form containing bioactive glass while in alternate embodiments, a dose of bioactive glass is provided to be incorporated into the bone graft prior to or during implantation into the surgical site.

Bone graft materials of the present invention that may be preferred exhibit high degrees of porosity. It is also preferred that the porosity occur in a broad range of effective pore sizes. In this regard, persons skilled in the art will appreciate that preferred embodiments of the invention may have, at once, macroporosity, mesoporosity, and microporosity. Macroporosity is characterized by pore diameters greater than about 100 µm and, in some embodiments, up to about 1000 µm to 2000 µm. Mesoporosity is characterized by pore diameters between about 100 µm and 10 µm, while microporosity occurs when pores have diameters below about 10 µm. It is preferred that macro-, meso-, and microporosity occur simultaneously and are interconnected in products of the invention. It is not necessary to quantify each type of porosity to a high degree. Rather, persons skilled in the art can easily determine whether a material has each type of porosity through examination, such as through the preferred methods of mercury intrusion porosimetry and scanning electron microscopy. While it is certainly true that more than one or a few pores within the requisite size range are needed in order to characterize a sample as having a substantial degree of that particular form of porosity, no specific number or percentage is called for. Rather, a qualitative evaluation by persons skilled in the art shall be used to determine macro-, meso-, and microporosity.

It will be appreciated that in some embodiments of the overall porosity of materials prepared in accordance with this invention be high. This characteristic is measured by pore volume, expressed as a percentage. Zero percent pore volume refers to a fully dense material, which, perforce, has no pores at all. One hundred percent pore volume cannot meaningfully exist since the same would refer to "all pores" or air. Persons skilled in the art understand the concept of pore volume, however and can easily calculate and apply it. For example, pore volume may be determined in accordance with Kingery, W. D., Introduction to Ceramics, Wiley Series on the Science and Technology of Materials, 1st Ed., Hollowman, J. H., et al. (Eds.), Wiley & Sons, 1960, p. 409-417, who provides a formula for determination of porosity. Expressing porosity as a percentage yields pore volume. The formula is: Pore Volume=(1−fp) 100%, where fp is fraction of theoretical density achieved.

Porosity can be measured by methods known in the art such as helium pycnometry. This procedure determines the density and true volume of a sample by measuring the pressure change of helium in a calibrated volume. A sample of known weight and dimensions is placed in the pycnometer, which determines density and volume. From the sample's mass, the pycnometer determines true density and volume. From measured dimensions, apparent density and volume can be determined. Porosity of the sample is then calculated using (apparent volume measured volume)/apparent volume. Porosity and pore size distribution may also be measured by mercury intrusion porosimetry, another method known in the art.

Pore volumes in excess of about 30% may be achieved in accordance with this invention while materials having pore volumes in excess of 50% or 60% may also be routinely attainable. Some embodiments of the invention may have pore volumes of at least about 70%. Other embodiments have pore volumes in excess of about 75% or about 80%. Pore volumes greater than about 85% are possible, as are volumes of about 90%. In preferred cases, such high pore volumes are attained while also attaining the presence of macro- meso-, and microporosity as well as physical stability of the materials produced. It is believed to be a great advantage to prepare graft materials having macro-, meso-, and microporosity simultaneously with high pore volumes that also retain some compression resistance and flexibility, moldability, or flowability when wetted.

Due to the high porosity and broad pore size distribution (1 μm-1000 μm) of the present invention graft, the implant is not only able to wick/soak/imbibe materials very quickly, but is also capable of retaining them. A variety of fluids could be used with the present invention including blood, bone marrow aspirate, saline, antibiotics and proteins such as bone morphogenetic proteins (BMPs). Materials of the present invention can also be imbibed with cells (e.g., fibroblasts, mesenchymal, stromal, marrow and stem cells), platelet rich plasma, other biological fluids, and any combination of the above. Bone grafts of the present invention actually hold, maintain, and/or retain fluids once they are imbibed, allowing for contained, localized delivery of imbibed fluids. This capability has utility in cell-seeding, drug delivery, and delivery of biologic molecules as well as in the application of bone tissue engineering, orthopaedics, and carriers of pharmaceuticals.

Wettability determines the amount of fluid taken up by sample material and if the material absorbs an appropriate amount of fluid within a specified time. Pieces of the material are randomly selected, weighed, and placed in a container of fluid for 120 seconds. If the samples adequately take up fluid, they are then weighed again to determine the percentage of mass increase from fluid absorption.

Some embodiments exhibit a wettability wherein bone graft material becomes fully saturated within 120 seconds with at least a 100% mass increase. In some embodiments, the graft material experiences a 150% mass increase and yet, in others, an approximately 200%-300% mass increase. Fluids that may be used in the present invention may be bone marrow aspirate, blood, saline, antibiotics and proteins such as bone morphogenetic proteins (BMPs) and the like.

It is preferred that flexible grafts of the present invention will be able to wick and hold fluids, even under compression. It is preferred that moldable embodiments will be able to wick and hold fluids, even in a wet environment. For example, if a wetted, flexible graft is placed on mesh suspended above a weigh boat and is challenged with a 500 g weight, it is preferred that the graft maintain a mass of fluid at least about 95% of the mass of the graft or about equivalent to the mass of the graft. If a wetted, moldable graft of the invention is placed in fluid, it is preferred that the graft maintains as a continuous object and does not swell substantially larger in size than its original dimensions. In some instances, the graft does not swell in size greater than about 50% more than its original dimensions, by qualititative assessment. If a wetted, moldable graft of the invention is compressed, it is preferred that the graft maintain a mass of fluid at least about 85% of the mass of the graft or about equivalent to the mass of the graft.

In accordance with the present invention, some bone graft materials disclosed may partially comprise materials, or morsels, resulting from an oxidation-reduction reaction. These materials may be produced by methods comprising preparing an aqueous solution of a metal cation and at least one oxidizing agent. The solution is augmented with at least one soluble precursor anion oxidizable by said oxidizing agent to give rise to the precipitant oxoanion. The oxidation-reduction reaction thus contemplated is conveniently initiated by heating the solution under conditions of temperature and pressure effective to give rise to said reaction. In accordance with preferred embodiments of the invention, the oxidation-reduction reaction causes at least one gaseous product to evolve and the desired intermediate precursor mineral to precipitate from the solution. In accordance with certain preferred embodiments of the present invention, a reactive blend in accordance with the invention may be imbibed into a material that is capable of absorbing it to produce a porous mineral. It may be preferred that the material have significant porosity, be capable of absorbing significant amounts of the reactive blend via capillary action, and that the same be substantially inert to reaction with the blend prior to its autologous oxidation-reduction reaction.

The intermediate precursor mineral thus prepared can either be used "as is" or can be treated in a number of ways. Thus, it may be heat-treated greater than about 800° C. or, preferably, greater than about 1100° C. in accordance with one or more paradigms to give rise to a preselected crystal structure or other preselected morphological structures therein. In accordance with preferred embodiments, the oxidizing agent is nitrate ion and the gaseous product is a nitrogen oxide, generically depicted as NOx(g). It is preferred that the precursor mineral provided by the present methods be substantially homogenous. As used in this context, substantially homogenous means that the porosity and pore size distribution throughout the precursor mineral is the same throughout.

In accordance with other preferred embodiments, the intermediate precursor mineral provided by the present invention may be any calcium salt. Subsequent modest heat treatments convert the intermediate material to, e.g., novel monophasic calcium phosphate minerals or novel biphasic β-tricalcium phosphate (β-TCP)+type-B, carbonated apatite (c-HAp) [β-$Ca_3(PO_4)_2$+$Ca_5(PO_4)_{3-x}(CO_3)x(OH)$] particulates. More preferably, the heat treatment converts the intermediate material to a predominantly β-TCP material.

It will be appreciated that the porosity is similar to that of inorganic shaped bodies disclosed in the '519 and '246 patents. The bone graft materials of the present invention are indeed improvements on the shaped bodies disclosed in the '519 and '246 patents. For some embodiments of the present invention, the shaped bodies of the '519 and '246 patents are modified using various natural and synthetic polymers, film forming materials, resins, slurries, aqueous mixtures, pre-polymers, organic materials, metals, and other adjuvants. Materials such as wax, glycerin, gelatin, polycaprolactone, pre-polymeric materials such as precursors to various nylons, acrylics, epoxies, polyalkylenes, and the like, were caused to permeate all or part of the shaped bodies formed in accordance with the '519 and '246 patents. The soak and hold properties of some graft materials disclosed herein exhibit at least a 100% mass increase of blood. Many of the bone graft materials of the present invention have structural integrity with improved clinical handling when compared to the bodies of the '519 and '246 patents.

The bone graft materials may also have improved handling that can provide a unit dose delivery. The addition of collagen in the present invention graft material greatly enhances the ability of the product to be shaped or cut without crumbling. The graft materials may be shaped or cut using various instruments such as a scalpel or scissors. This feature finds utility in a variety of surgical applications, particularly since the bone graft can be formed "in situ" in an operating room to suit the needs of the patient in cases where the bone void to be filled is an irregular shape. Some graft materials disclosed may also be delivered into the bony site directly, shaped, and allowed to wick bodily fluids by an operator while during an operation.

Figure 11:
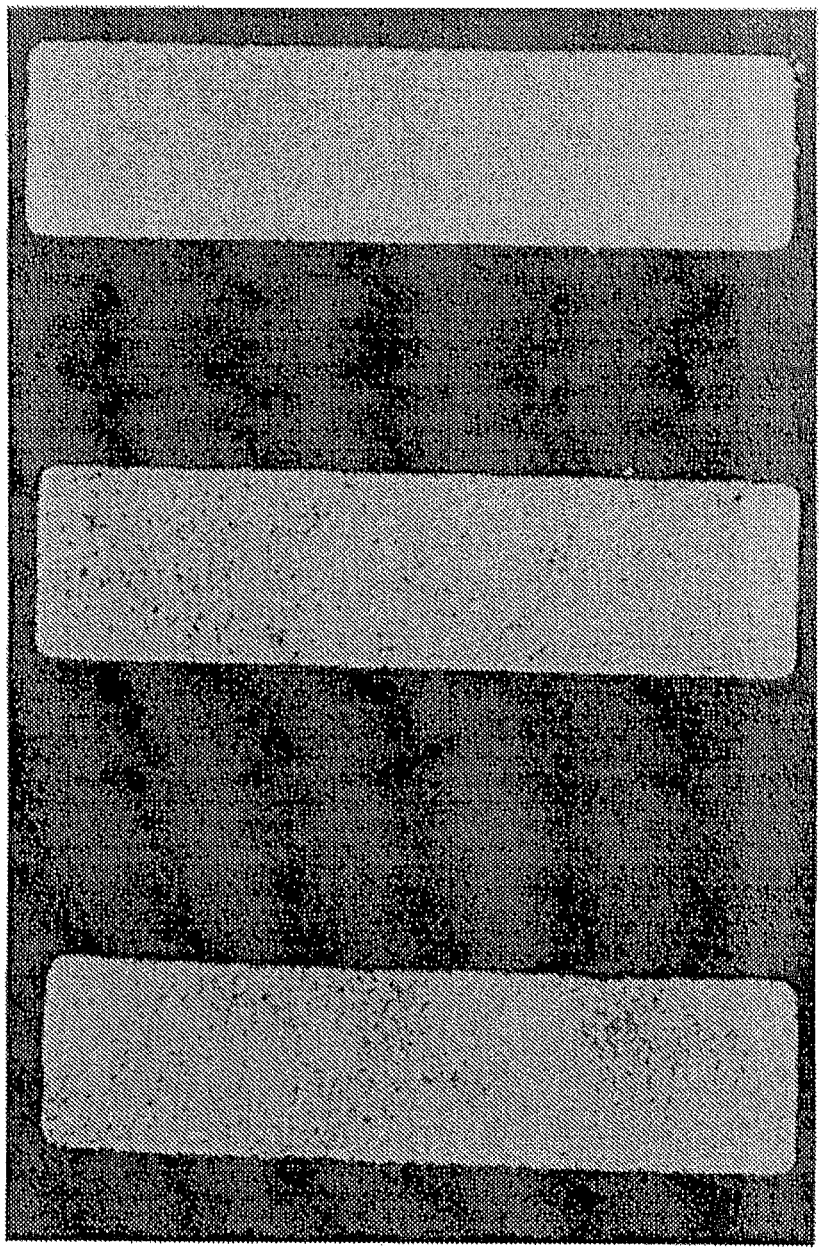
FIG. 11 are high resolution X-rays depicting the radiopacity of embodiments of the present invention as compared to synthetic bone graft material containing 0% bioactive glass (commercially available Vitoss® Foam Strip and labeled as "Commercial Foam").

Materials of the present invention are also radiopaque, as shown in FIG. 11. The bone graft materials may be sterilized and may be preferably gamma irradiated at a range of about 25 kGy to 40 kGy.

Bone graft materials of the present invention have osteoconductive and osteostimulatory properties. In certain embodiments, the addition of bioactive glass in the present invention enhances the ability of the product to foster bone growth. The bone graft materials of the present invention may also have osteoinductive properties.

Many of the embodiments disclosed herein are to fill bony voids and defects. It will be appreciated that applications for the embodiments of the present invention include, but are not limited to, filling interbody fusion devices/cages (ring cages, cylindrical cages), placement adjacent to cages (i.e., in front cages), placement in the posterolateral gutters in posterolateral fusion (PLF) procedures, backfilling the iliac crest, acetabular reconstruction and revision hips and knees, large tumor voids, use in high tibial osteotomy, burr hole filling, and use in other cranial defects. The bone graft material strips may be suited for use in PLF by placement in the posterolateral gutters, and in onlay fusion grafting. Additional uses may include craniofacial and trauma procedures that require covering or wrapping of the injured/void site. The bone graft material cylinders may be suited to fill spinal cages and large bone voids, and for placement along the posterolateral gutters in the spine.

Figures 13A, 13B, 13C:
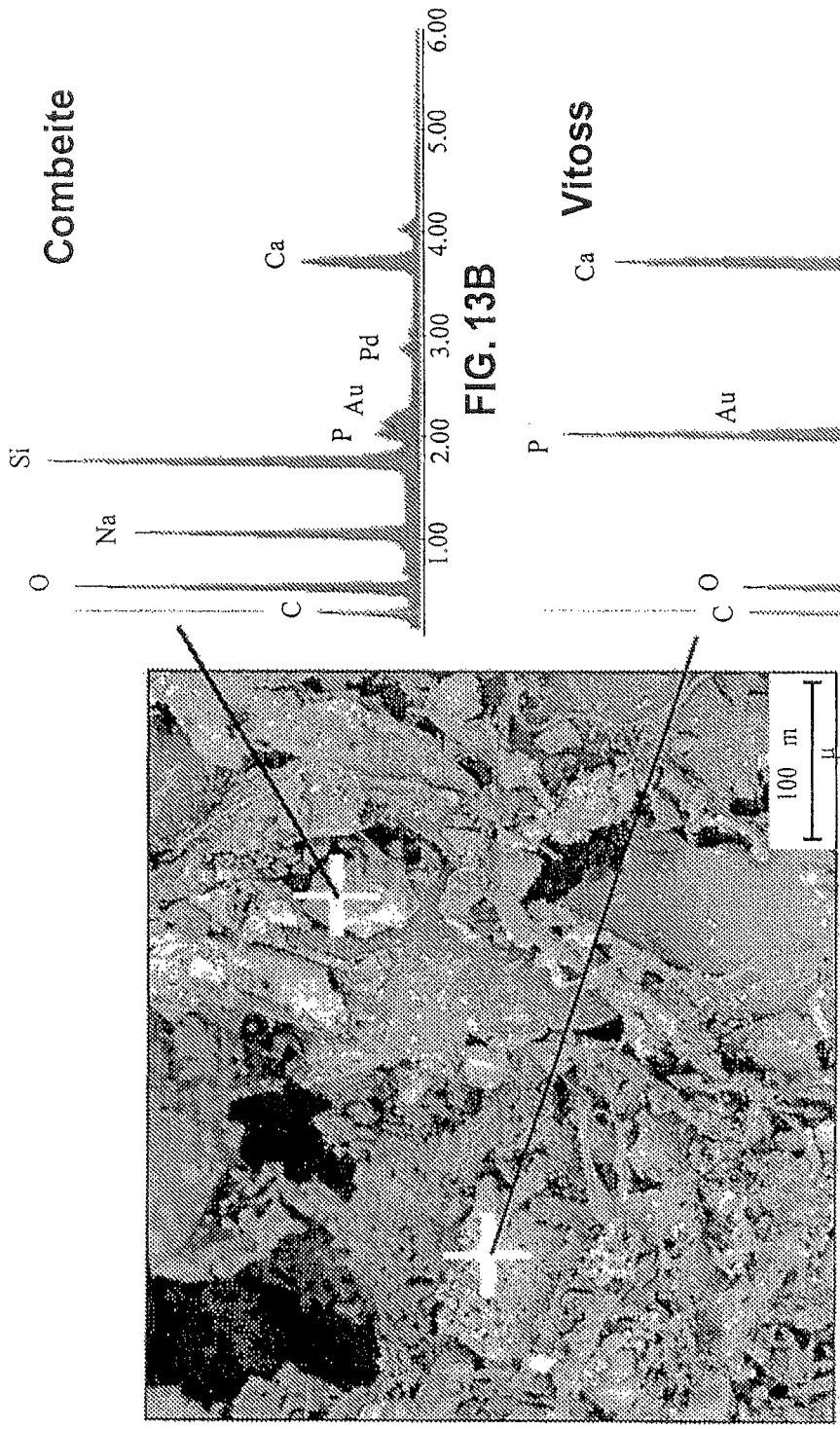
FIG. 13A depicts a SEM (250×, backscatter) of one embodiment of the present invention, comprising 80% by weight of calcium phosphate, 10% collagen, and 10% combeite glass-ceramic.
FIG. 13B depicts an elemental analysis of the combeite region.
FIG. 13C depicts an elemental analysis of the porous calcium phosphate region. Gold (Au) and palladium (Pd) are present as a result of the conductive coating applied to the specimen.

Scanning electron micrographs (SEMs) of certain embodiments of the present invention demonstrate the high porosity of these graft materials (see, for example, FIGS. 8-10, 12-14). FIGS. 12-14 further depict the morphology of certain embodiments of the present invention, highlighting the areas of porosity and areas of combeite glass-ceramic. FIGS. 13B and 13C show the elemental analyses of the porous and regions on one embodiment of the present invention.

Figure 3B:
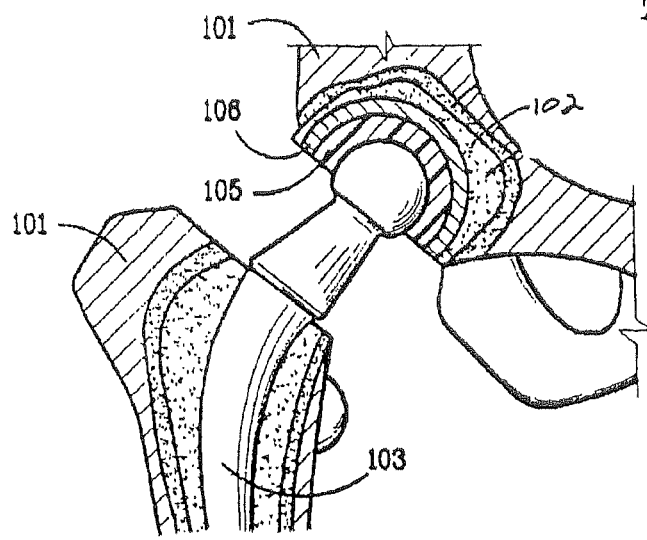
FIG. 3B depicts a semi-spherical form of the graft material 102 used to accommodate an artificial implant 103. The graft material 102 contains an acetabular cup 106, which holds a polyethylene cup 105, in this embodiment.
Figure 3A:
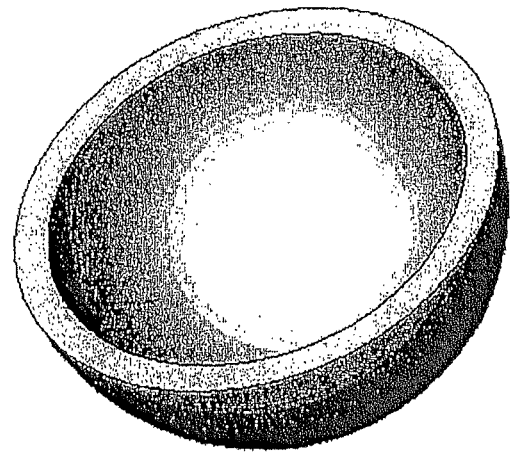
FIG. 3A illustrates one embodiment of the biocompatible graft material of the present invention in semi-spherical form used as a graft containment device.
Figure 4A:
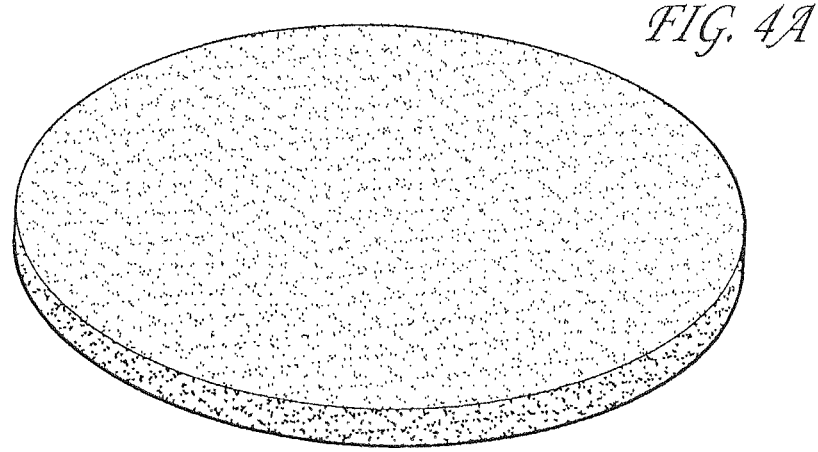
FIG. 4A illustrates the graft material of the present invention in disc form.
Figure 4B:
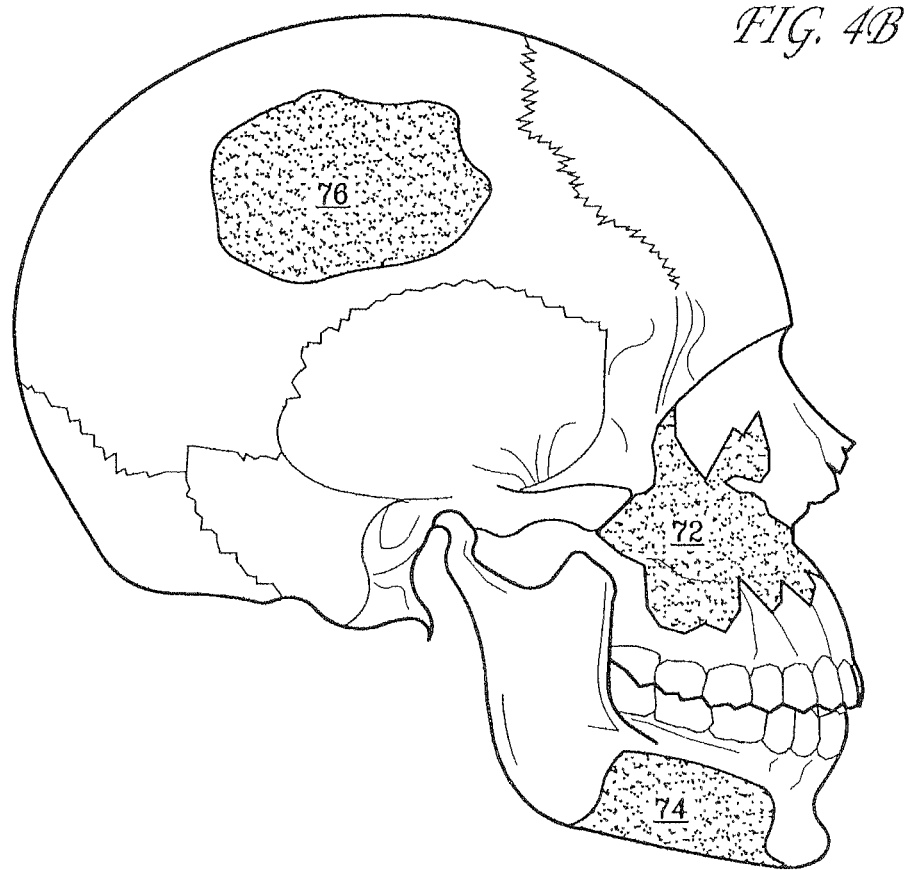
FIG. 4B illustrates another embodiment of the biocompatible graft material of the present invention used as a cranio-maxillofacial 76, zygomatic reconstruction 72, and mandibular implant 74.
Figure 5:
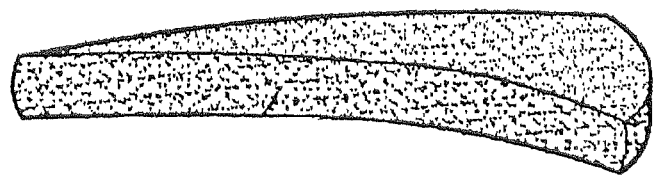
FIG. 5 illustrates one embodiment of a bone graft material described shaped into a block/wedge form and used as a tibial plateau reconstruction that is screwed, bonded, cemented, pinned, anchored, or otherwise attached in place.

Due to the wide range of applications for the embodiments of the present invention, it should be understood that the present invention graft material could be made in a wide variety of shapes and sizes via standard molding techniques. For instance, blocks and cylinders of the present invention may find utility in bone void filling and filling of interbody fusion devices; wedge shaped devices of the present invention may find utility in high tibial osteotomies; and strips may find utility in cranial defect repairs. Of particular interest, may be the use of some of the graft materials as semi-spherical (FIG. 3A), semi-tubular (FIGS. 7A-7C) or disc-shaped (FIG. 4A) strips for graft containment devices. An embodiment of the semi-spherical form 102 in use is depicted in FIG. 3B.

It will be appreciated that these shapes are not intended to limit the scope of the invention as modifications to these shapes may occur to fulfill the needs of one skilled in the art. The benefits of the graft containment materials that, for instance, may be used in acetabular reconstruction made from the present invention are several-fold. The graft materials may act as both a barrier to prevent migration of other implants or graft materials and serves as an osteoconductive resorbable bone graft capable of promoting bone formation. The graft containment device may be relatively non-load-bearing, or partially load-bearing, or may be reinforced to be fully load-bearing as described below. Depending on the form, the graft materials have barrier properties because it maintains its structural integrity.

Figure 6A:
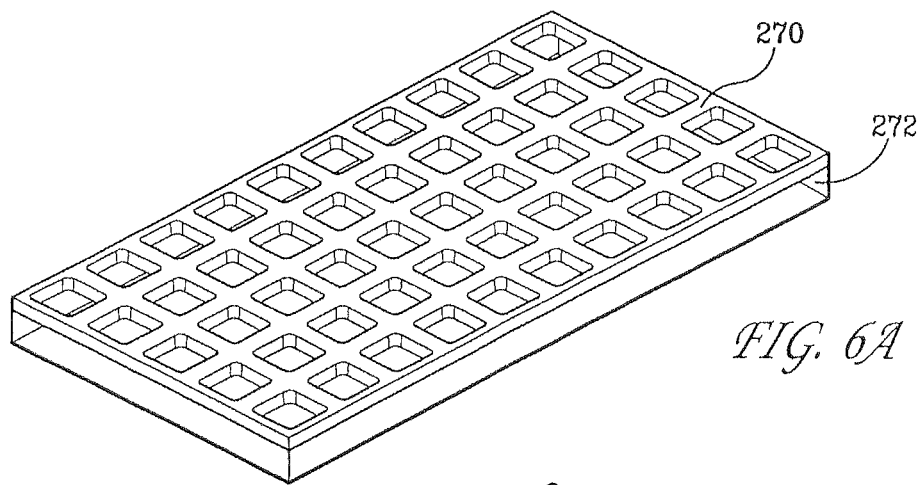
FIGS. 6A and 6B illustrate synthetic resorbable defect filling bone graft materials 272 for bone restoration having mesh 270 attached to one side.
Figure 6B:
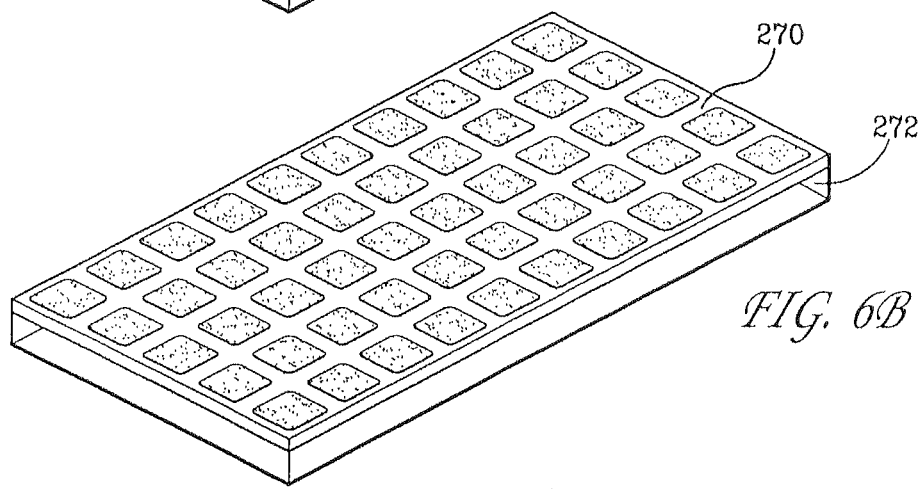
Figure 6C:
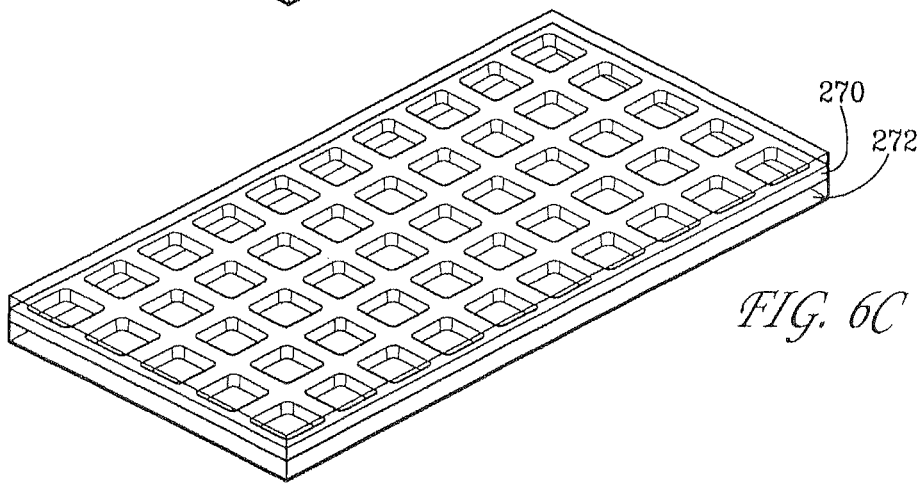
FIG. 6C depicts a synthetic resorbable defect filling bone graft material block in which the mesh 270 is sandwiched between the graft material 272.
Figure 7A:
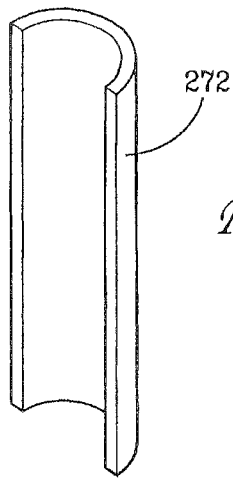
FIGS. 7A, 7B, and 7C illustrate an embodiment of the biocompatible graft material of the present invention in semi-tubular form used as a long bone reinforcement sleeve. As shown in the figures, the semi-tube may have a moon cross-section with a uniform thickness (FIG. 7A); or a crescent moon cross-section with a tapered radius that comes to a point (FIG. 7B) or a tapered radius that is rounded on the edges (FIG. 7C).
Figure 7B:
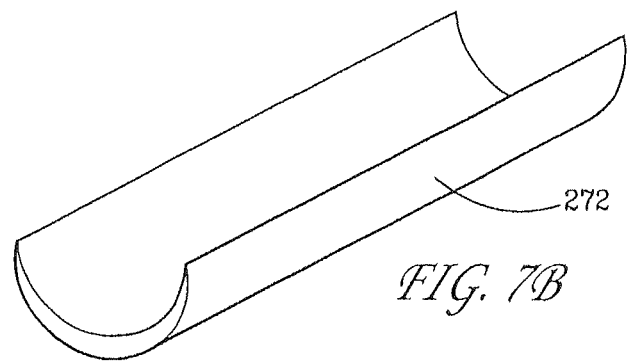
Figure 7C:
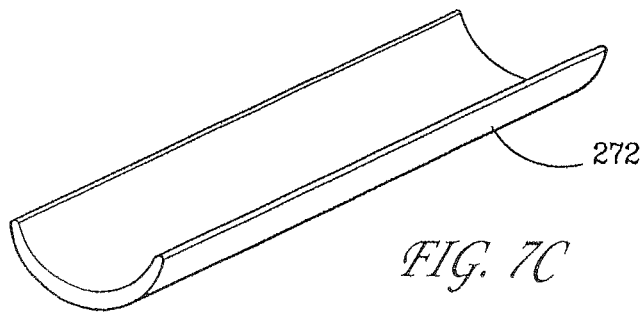
Figure 10:
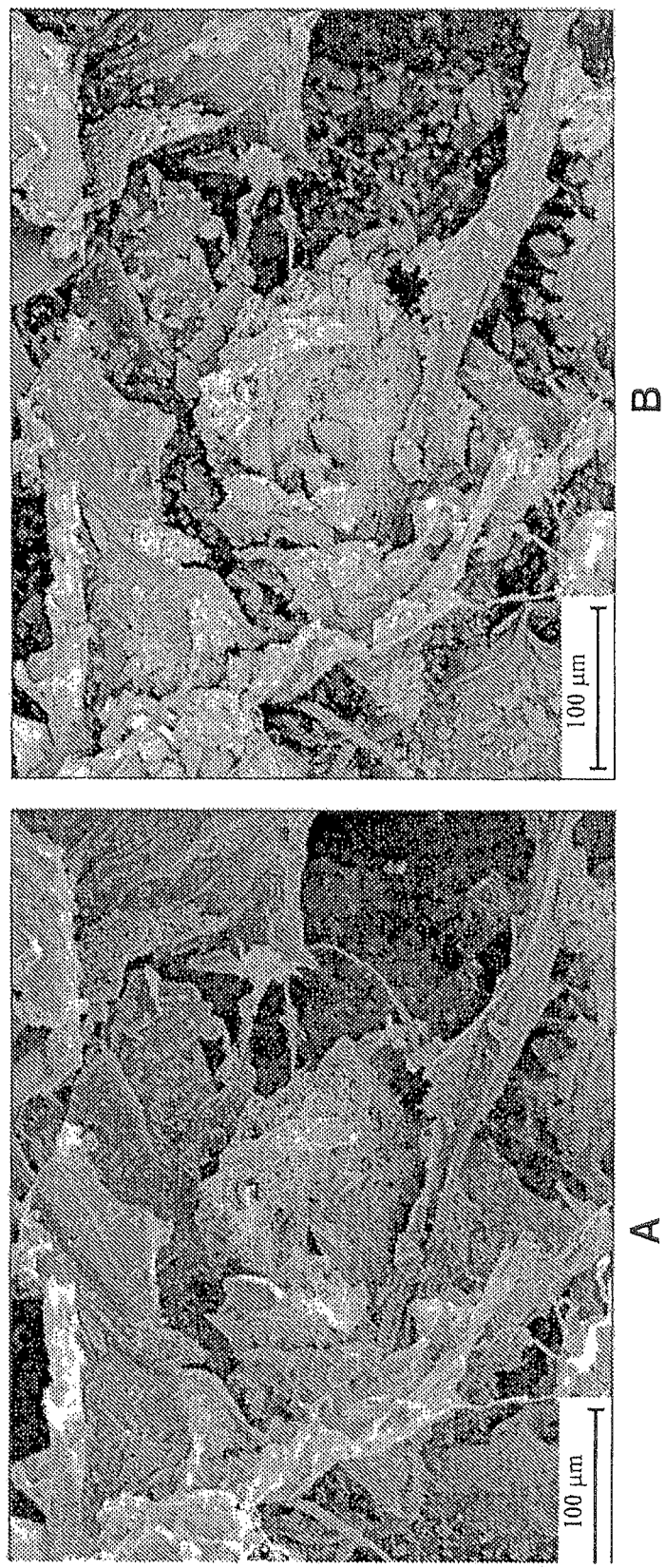
FIG. 10A is a SEM (secondary, 250×) of one embodiment of the bone graft material of the present invention, comprising 80% by weight of calcium phosphate, 10% collagen, and 10% combeite glass-ceramic.
FIG. 10B is a SEM (backscatter, 250×) of one embodiment of the bone graft material of the present invention, comprising 80% by weight of calcium phosphate, 10% collagen, and 10% combeite glass-ceramic.

In applications requiring graft materials with load-bearing capabilities, the graft materials of the present invention may have meshes or plates affixed. The meshes or plates may be of metal, such as titanium or stainless steel, or of a polymer or composite polymer such as polyetheretherketone (PEEK), or nitinol. As depicted in FIGS. 6A and 6B, a metallic mesh 270 may be placed to one side of the bone graft material 272 to add strength and load-bearing properties to the implant. In FIG. 6A, the mesh plate 270 sits affixed to one surface of the graft material 272. In FIG. 6B, the mesh plate 270 penetrates one surface of the graft material 272 with one side of mesh exposed on top. In FIG. 6C, the mesh plate 270 is immersed more deeply than in FIG. 6B within the graft material 272. FIGS. 7A-7C depict another embodiment of the graft material 272 in semi-tubular form. A mesh may be affixed to a surface for further support in long bone reinforcement. Due to the unique properties of the present invention graft material, the mesh may be affixed in the body using sutures, staples, screws, cerclage wire or the like.

One skilled in the art may place the mesh in any location necessary for a selected procedure in a selected bodily void. For instance, a composite of mesh and graft material could be used in a craniomaxillofacial skull defect with the more pliable graft surface being placed in closer proximity to the brain and the more resilient mesh surface mating with the resilient cortical bone of the skull. In this manner, the mesh or plate may be affixed to one side of the graft material. Alternatively, the mesh or plate may be affixed to both sides of the graft material in sandwich fashion. Likewise, graft material could be affixed to both sides of the mesh or plate. In some embodiments, the mesh may be immersed within the graft material. The meshes may be flat or may be shaped to outline the graft material such as in a semi-spherical, semi-tubular, or custom form. These embodiments may be unique due to their integral relation between the graft material and the mesh. This is contrary to other products in the field in which the graft material is placed adjacent to the structural implant or, in the case of a cage, within the implant.

In accordance with the present invention, another embodiment provides a bone graft for long bone reinforcement comprising a biocompatible, resorbable semi-tubular shape, or sleeve, of β-tricalcium phosphate, collagen, and a bioactive glass, the entire graft having interconnected macro-, meso-, and microporosity. A mesh may be affixed to the surface of the sleeve or may be immersed in the sleeve. The mesh may be made of titanium, stainless steel, nitinol, a composite polymer, or polyetheretherketone. The cross-section of the sleeve may be in the shape of a crescent shape moon (FIG. 7B).

In other embodiments, there is a graft for the restoration of bone in the form of a shaped body, the shaped body comprising β-tricalcium phosphate, collagen, and a bioactive glass, the material of the graft having interconnected macro-, meso-, and microporosity; the body shape being selected to conform generally to a mammalian, anatomical bone structure. The shapes will vary depending on the area of the body being repaired. Some basic shapes may be a disk, semi-sphere, semi-tubular, or torus. In some embodiments, the shape will conform generally to the acetabulum.

Other graft materials of the present invention having load-bearing capabilities may be open framed, such that the bone graft material is embedded in the central opening of the frame. The frame may be made of a metal such as titanium or of a load-bearing resorbable composite such as PEEK or a composite of some form of poly-lactic acid (PLA). In the case of the latter, the acid from the PLA co-acts, or interacts with the calcium phosphate of the embedded bone graft material to provide an implant with superior resorption features.

The graft materials can also be imbibed with any bioabsorbable polymer or film-forming agent such as polycaprolactones (PCL), polyglycolic acid (PGA), poly-L-Lactic acid (PL-LA), polysulfones, polyolefins, polyvinyl alcohol (PVA), polyalkenoics, polyacrylic acids (PAA), polyesters and the like. The resultant graft material is strong, carveable, and compressible. The grafts of the present invention coated with agents such as the aforementioned may still absorb blood.

In another embodiment of the present invention, the graft materials may be used as an attachment or coating to any orthopaedic implant such as a metal hip stem, acetabular component, humeral or metatarsal implant, vertebral body replacement device, pedicle screw, general fixation screw, plate or the like. The coating may be formed by dipping or suspending the implant for a period of time in a substantially homogenous slurry of calcium phosphate, collagen, and bioactive glass and then processing via freeze-drying/lypholization and crosslinking techniques. As used in this context, substantially homogenous means that the ratio of elements within the slurry is the same throughout. Alternatively, a female mold may be made of the implant and the slurry may be poured into the mold and processed, as described above, to form the coating.

In yet another embodiment of the present invention, the graft material may be shredded or cut into small pieces. These smaller shredded pieces could then be used as filler or could be placed in a syringe body. In this fashion, fluids could be directly aspirated into or injected into the syringe body thereby forming a cohesive, shapeable bone graft mass "in situ" depending upon the application requirements. The shredded pieces find particular use as filler for irregular bone void defects. Further, unlike traditional bone graft substitutes they are highly compressible and therefore can be packed/impacted to insure maximum contact with adjacent bone for beneficial healing.

EXAMPLES

Example 1

Wettability

Dry test samples measuring 25×100×4 mm were weighed and then dipped ("soaked") in a saline solution for 30 seconds. The weight of the soaked sample was measured. The results of these tests are depicted in Table 1.

TABLE 1

| Sample No. | Calcium phosphate (Vitoss ®): Combeite g-c:Collagen | Dry Weight (g) | Wet Weight (g) | Δ (g) | Mass Increase |
|---|---|---|---|---|---|
| Test Sample 1 | 80:5:15 | 4.4486 | 13.967 | 9.5184 | 214% |
| Test Sample 2 | 80:10:10 | 5.804 | 14.526 | 8.722 | 150% |
| Test Sample 3 | 80:5:15 | 3.391 | 12.44 | 9.049 | 267% |
| Test Sample 4 | 80:10:10 | 4.33 | 13.589 | 9.259 | 214% |
| Control | 100:0:0 | 4.6742 | 14.052 | 9.3778 | 201% |

Example 2

Assessment of Bioactivity

Bioactivity analysis was conducted on scaffold formulations comprising calcium phosphate, collagen, and bioactive glass in weight ratios of 80:10:10 and 80:15:5. In vitro apatite formation was assessed using SBF, comprising the salts of $Na_2SO_4$, $K_2HPO_4.3H_2O$, $NaHCO_3$, $CaCl_2$, $MgCl_2.6H_2O$, NaCl, and KCl. These reagents were dissolved in deionized water and buffered to a pH of approximately 7.3 using Tris (hydroxyl-methyl-amino-methane) and hydrochloric acid. The ionic concentration of the resultant solution closely resembles that of human blood plasma.

A 1×1 cm specimen of each scaffold formulation was immersed in 20 ml of SBF and incubated at 37° C. At specified time points of 1, 2, and 4 weeks the samples were removed from solution, rinsed with distilled water and acetone, and dried in a dessicator. Bioactivity assessment was carried out using scanning electron microscopy (SEM) and energy dispersive spectroscopy (EDS) to identify changes in surface morphology and composition, respectively.

Example 3

Figure 15A:
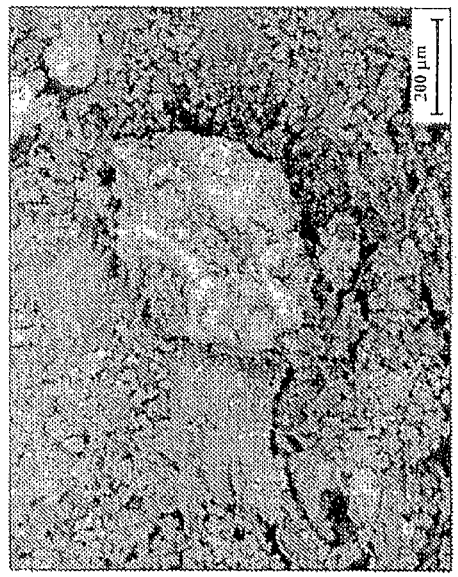
FIGS. 15A, 15B, and 15C are SEMS of one embodiment of the present invention, comprising 80% by weight of calcium phosphate, 15% collagen, and 5% combeite glass-ceramic, after immersion in SBF for four weeks.
Figure 15B:
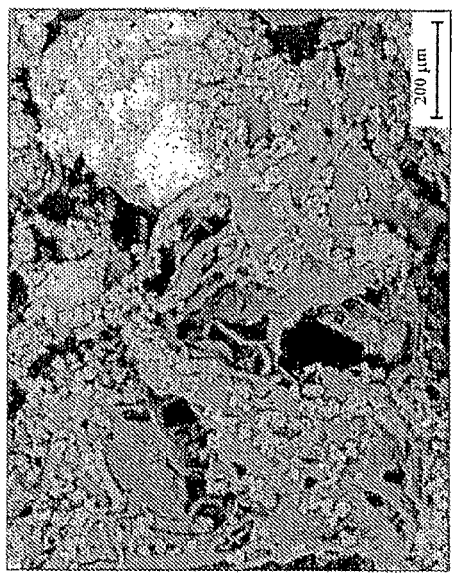
Figure 15C:
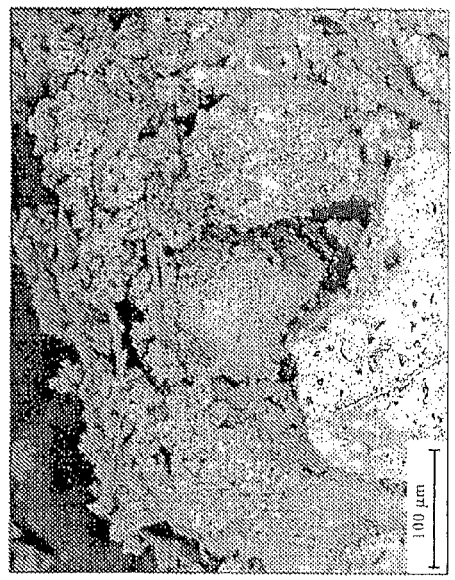
Figure 16B:
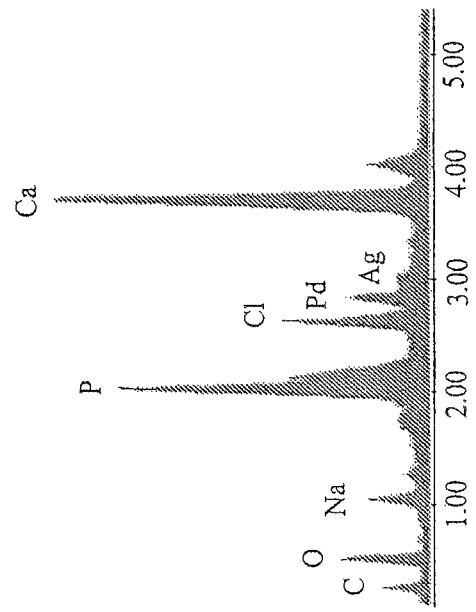
FIG. 16B represents the EDAX spectra of the boxed area of FIG. 16A, representing new calcium phosphate growth, based on distinct morphology (differentiable than the calcium phosphate of the existing bone graft).
Figure 16A:
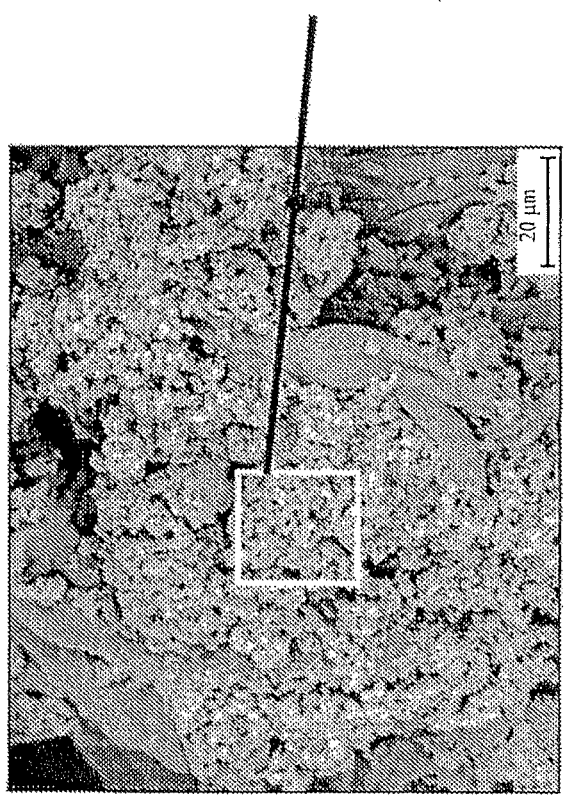
FIG. 16A is a SEM (magnified 1000×) of one embodiment of the present invention, comprising 80% by weight of calcium phosphate, 15% collagen, and 5% combeite glass-ceramic, after immersion in SBF for four weeks.

Bioactivity of Calcium
Phosphate:Collagen:Bioactive Glass Bone Graft
Substitutes (80:15:5) at 4 Weeks A sample of calcium phosphate, collagen, and bioactive glass (80:15:5) was immersed in SBF as per the methodology described in Example 2 for 4 weeks. After 4 weeks, SEM and EDAX spectra were taken. As seen in FIGS. 15, 16A, and 17A, new calcium phosphate formation can be identified based on its distinct morphology, as compared to the SEMs of samples prior to SBF immersion. Confirmation of new calcium phosphate formation was confirmed by EDAX spectra (FIGS. 16B, 17B-D). FIG. 16B shows the EDAX spectra of the new growth, confirming its calcium phosphate composition. As further demonstrated in FIGS. 17B and 17D, the new growth has a morphology and associated EDAX spectra distinct from the Vitoss. The EDAX spectra shown in FIG. 17C confirms the collagen strands of the base bone graft substitute visible in FIG. 17A.

Example 4

Figure 18B:
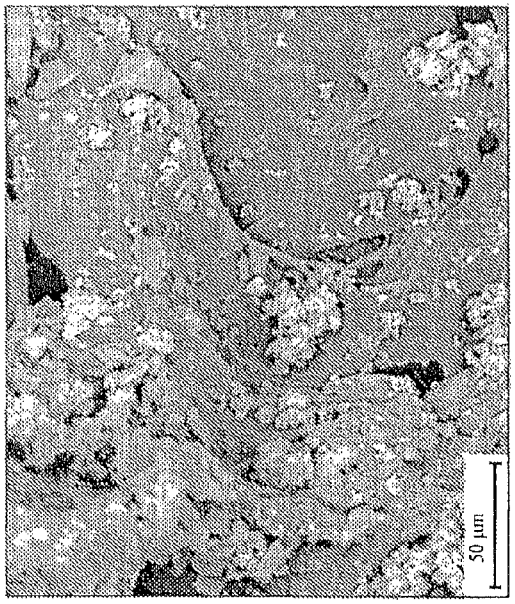
FIGS. 18A, 18B, and 18C are SEMS of one embodiment of the present invention, comprising 80% by weight of calcium phosphate, 10% collagen, and 10% combeite glass-ceramic, after immersion in SBF for four weeks.
Figure 18C:
Figure 18A:
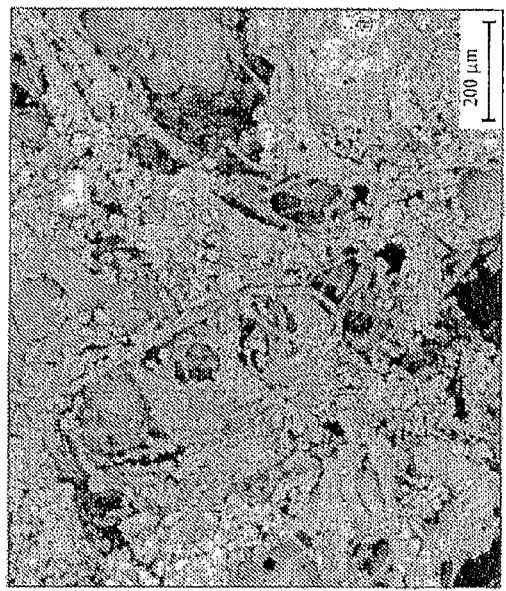

Bioactivity of Calcium
Phosphate:Collagen:Bioactive Glass Bone Graft
Substitutes (80:10:10) at 4 Weeks A sample of calcium phosphate, collagen, and bioactive glass (80:10:10) was immersed in SBF as per the methodology described in Example 2 for 4 weeks. After 4 weeks, SEM and EDAX spectra were taken. As seen in FIGS. 18, and 19A, new calcium phosphate formation can be identified based on its distinct morphology, as compared to the SEMs of samples prior to SBF immersion (see FIGS. 8-10, 12-14). Confirmation of new calcium phosphate formation was confirmed by EDAX spectra (FIGS. 19C). An area of combeite glass-ceramic (part of the base bone graft substitute) is confirmed by the EDAX spectra shown in FIG. 19B.

Example 5

Bioactivity Assessment of Bioactive Glass: Combeite Glass-Ceramic

Bone graft materials containing calcium phosphate, collagen, and combeite glass-ceramic particles were immersed in SBF for 7 days. SEM images were used to assess the formation of calcium phosphate on the glass surface. As seen in FIG. 20, the glass particles immersed in SBF for 7 days (FIG. 20B) show calcium phosphate development on the surface, indicative of the bioactive nature of the glass-ceramic. FIG. 20A shows an SEM of unreacted combeite glass-ceramic for comparison.

Example 6

Bioactivity Testing of Multiple Formulations of Calcium Phosphate, Collagen, and Bioactive Glass Samples of bone graft comprised of calcium phosphate, collagen and bioactive glass were prepared and tested for bioactivity. The calcium phosphate in each of the samples was porous β-tricalcium phosphate which is sold under the commercial name Vitoss® (Orthovita, Inc., Malvern, Pa.), and the bioactive glass used in each sample was combeite glass-ceramic. The formulations shown in Table 2 were tested:

TABLE 2

Composition of Control and Test Articles (by weight %)

|  | 0% glass | 10% glass | 20% glass | 40% glass | 80% glass |
| --- | --- | --- | --- | --- | --- |
| Vitoss | 80 | 80 | 70 | 50 | 10 |
| Combeite (<53 um) | 0 | 10 | 20 | 40 | 80 |
| Type I Collagen | 20 | 10 | 10 | 10 | 10 |

Table 3 shows the composition of the test articles in Table 2 by volume %. The assumptions for the volume % calculations were as follows: Bulk density of Vitoss® b-TCP (fully dense) is 3 g/cc, bulk density of combeite glass-ceramic is 2.84 g/cc, bulk density of collagen is 1.1 g/cc, and uniform mixing/distribution.

TABLE 3

Composition of Control and Test Articles (by volume %)

|  | 0% glass | 10% glass | 20% glass | 40% glass | 80% glass |
| --- | --- | --- | --- | --- | --- |
| Vitoss | 59 | 68 | 59 | 42 | 8 |
| Combeite g-c (<53 um) | 0 | 9 | 18 | 35 | 69 |
| Type I Collagen | 41 | 23 | 23 | 23 | 22 |

For the study, 6×4×10 mm samples were suspended by nylon fishing line from the lid of a sealed plastic cup and were immersed in 150 mL of SBF and kept on a rotating plate in a 37 C incubator. The SBF was not exchanged in any of the samples that were removed on or before Day 14. On Day 15, solution exchange occurred for the remaining 28 day samples. At days 1, 3, 7, 14, and 28, n=1 of each formulation was removed. Each sample was rinsed 3 times with water and once with acetone. Samples were stored in small glass vials in a dessicator. After drying in a dessicator for at least a day, each sample was cut in half with a razor blade and was mounted on a sample stub such that an exterior surface was exposed for analysis. Samples were sputter coated with Au-Pd using 60-80 mTorr and a 15-20 mA pulse.

Figure 21:
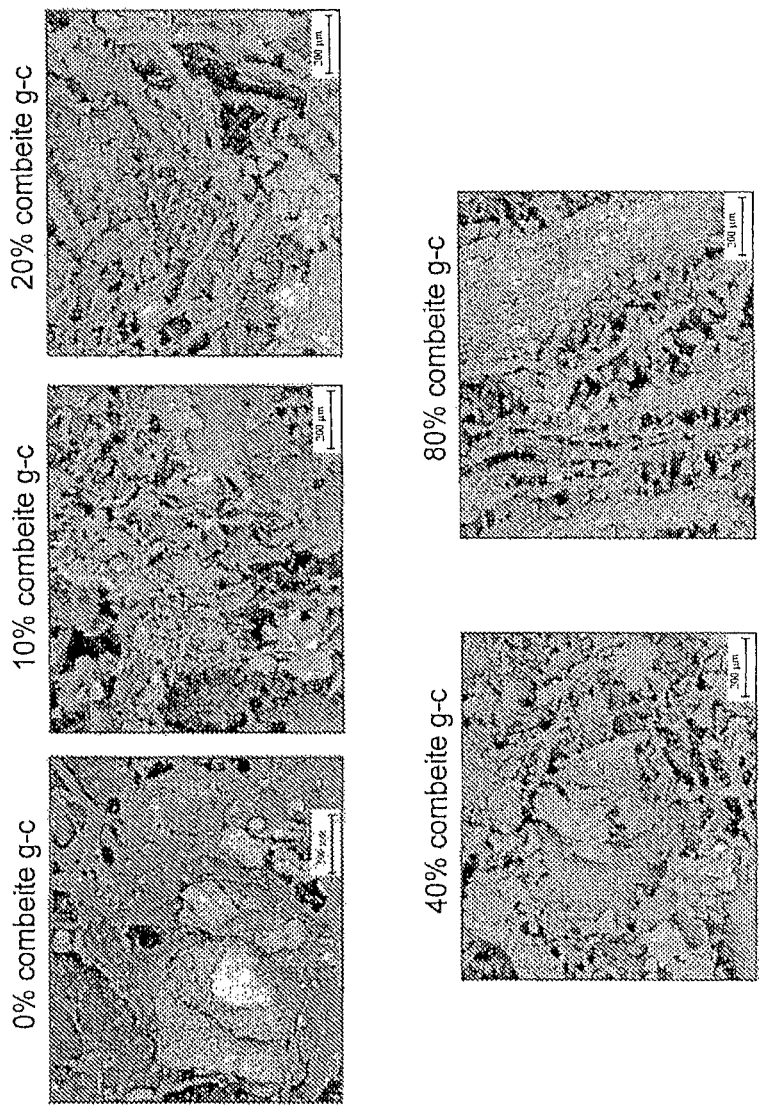
FIG. 21 depicts representative SEM images (100× magnification) of examples of bone grafts in accordance with embodiments of the present invention containing calcium phosphate, collagen, and 0%, 10%, 20%, 40%, or 80% by weight of combeite glass-ceramic ("combeite g-c").
Figure 22:
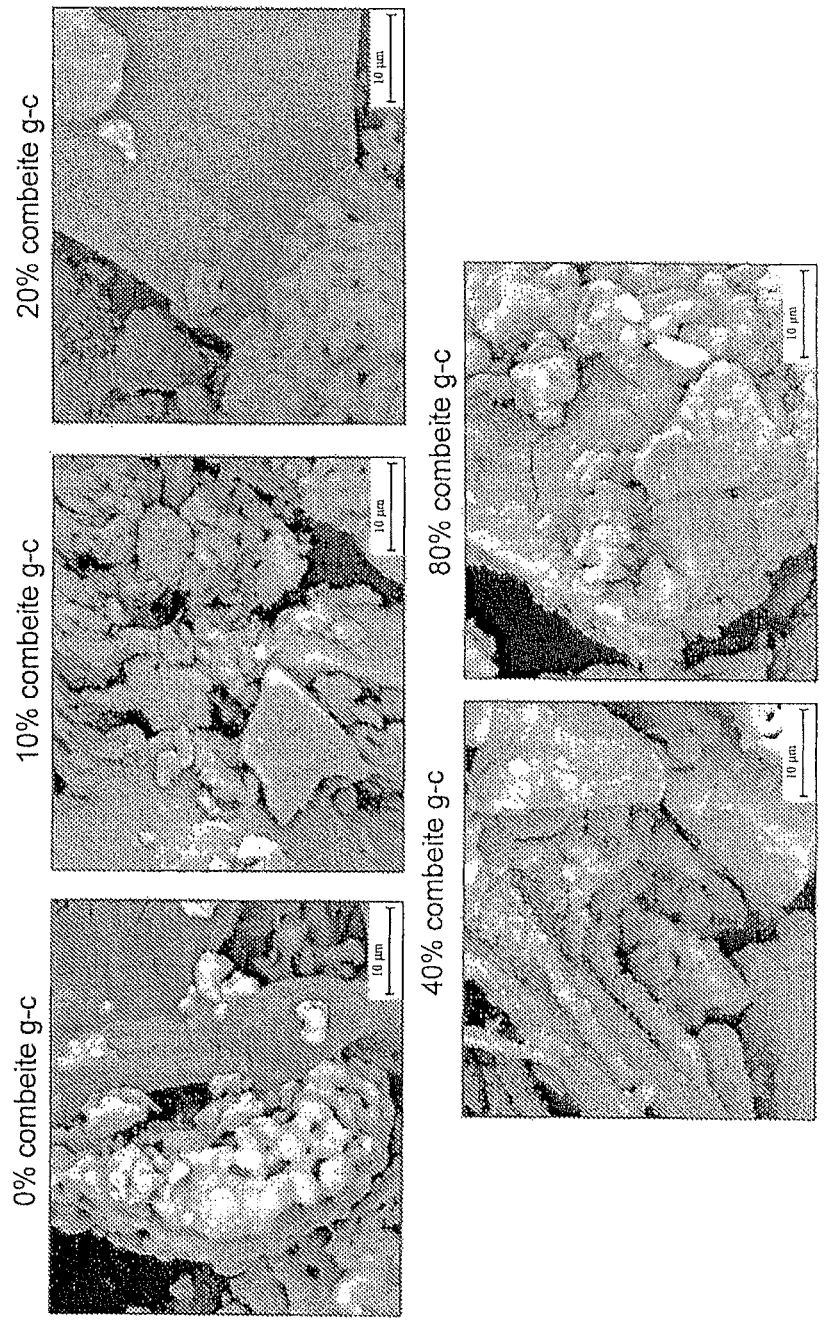
FIG. 22 depicts representative SEM images (2500× magnification) of examples of bone grafts in accordance with embodiments of the present invention containing calcium phosphate, collagen, and 0%, 10%, 20%, 40%, or 80% by weight of combeite glass-ceramic after 1 day in simulated body fluid (SBF).

All samples were imaged in backscatter mode. The SEM images were used to morphologically identify new calcium phosphate growth. No calcium phosphate growth was observed at any time point on the samples which did not contain bioactive glass (0% combeite glass-ceramic samples). These results confirm the suitability of the test method, as solution does not spontaneously precipitate growth onto the surface of these non-bioactive samples. Representative figures of unreacted formulations can be seen in FIG. 21 (Day 0, 100× magnification). All components could be seen in every formulation. Representative figures of all formulations after 1 day in SBF are shown in FIG. 22 (Day 1, 2500× magnification). Combeite glass-ceramic particles in all formulations have a fuzzy surface texture as compared to those from Day 0. In the 40% formulation, the newly formed calcium phosphate layer can be seen spreading from the bioactive glass particles onto adjacent collagen strands. In the 80% formulation, most of the bioactive glass particles are already covered in calcium phosphate which has begun to spread onto surrounding material.

By Day 3 (data not shown), in all glass-containing formulations, a layer of calcium phosphate has formed and appears to be spreading, with the 20 and 40% formulations having growth that is developed and widespread. The 80% formulation showed extensive calcium phosphate growth over the surface of the scaffold. Compositional analyses (EDS spectra, data not shown) confirmed that the layers were composed of calcium phosphate.

Figure 23:
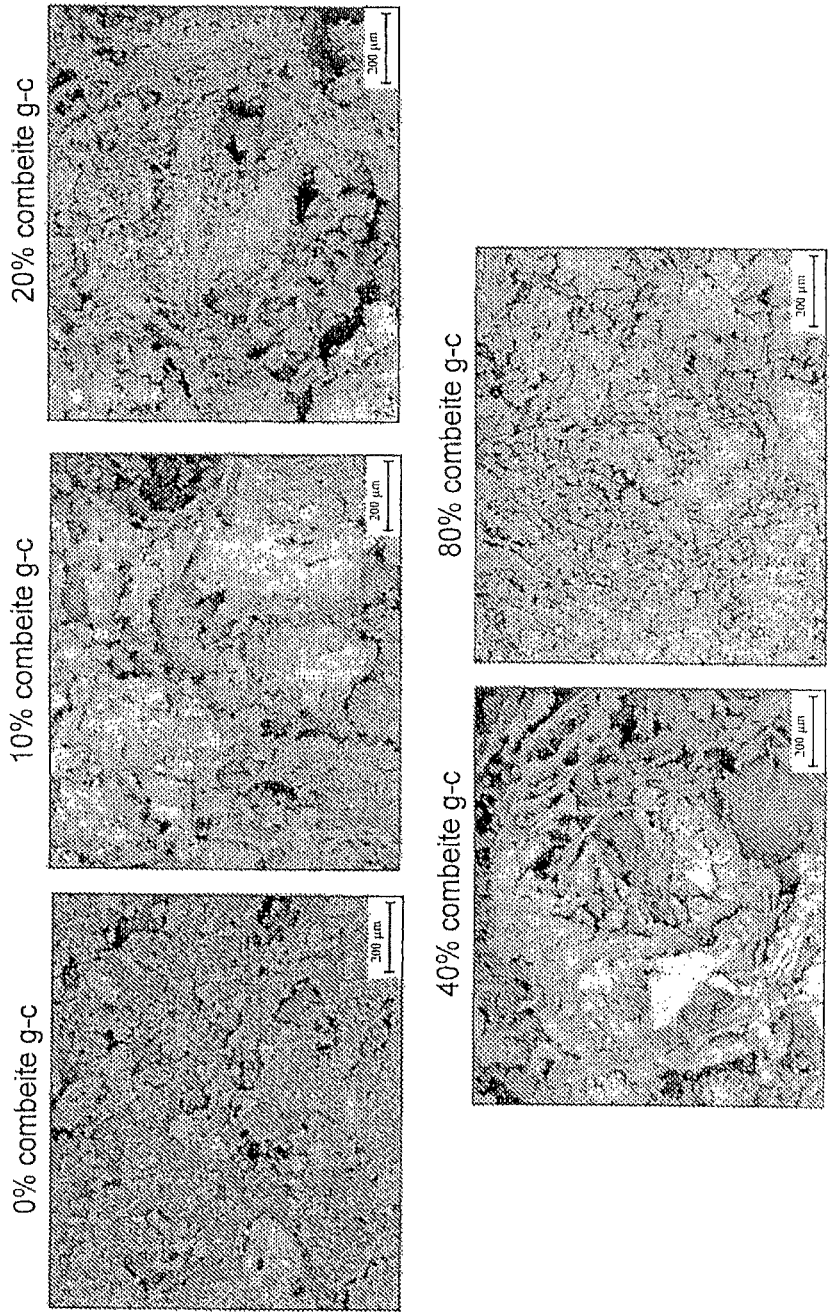
FIG. 23 depicts representative SEM images (100× magnification) of examples of bone grafts in accordance with embodiments of the present invention containing calcium phosphate, collagen, and 0%, 10%, 20%, 40%, or 80% by weight of combeite glass-ceramic after 7 days in SBF.
Figure 24:
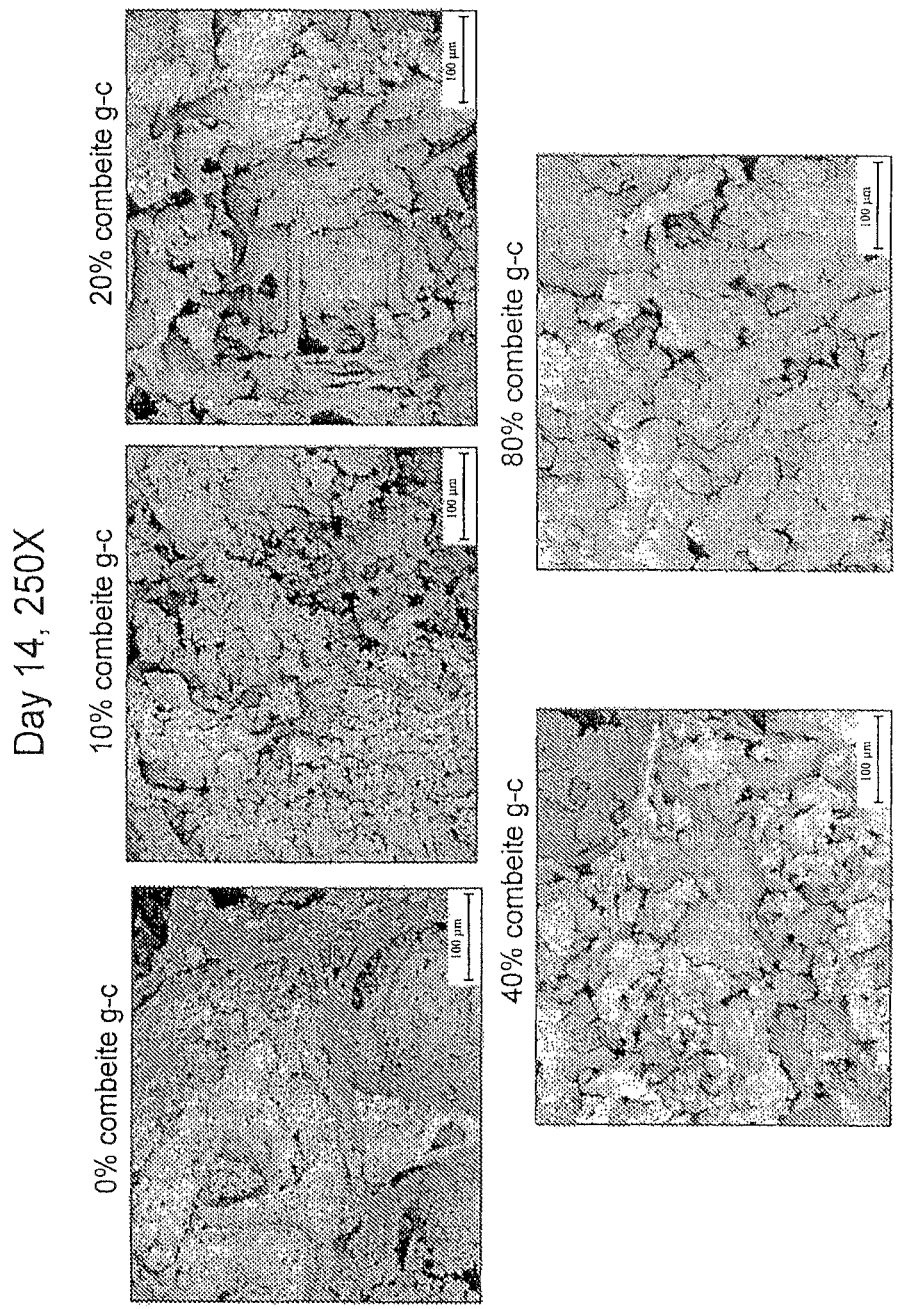
FIG. 24 depicts representative SEM images (250× magnification) of examples of bone grafts in accordance with embodiments of the present invention containing calcium phosphate, collagen, and 0%, 10%, 20%, 40%, or 80% by weight of combeite glass-ceramic after 14 days in SBF.

At Day 7 (FIG. 23), all glass-containing formulations show continued growth of the calcium phosphate layer. The 40% and 80% formulations both appear to have a continuous calcium phosphate layer covering virtually the entire surface of the samples. FIG. 24 shows representative images depicting well-developed calcium phosphate growth which covers virtually the entire surface of all glass-containing formulations at Day 14. Day 28 calcium phosphate growth on all glass-containing samples looks similar to Day 14 and appears mature and widespread (data not shown).

In general, greater bioactive glass content results in faster and more widespread calcium phosphate formation.

It is also noted that a test article containing about 23% by volume of collagen was pyrolized to burn off the collagen. The volume percent of the residual inorganic component was about 77%, consistent with the volume percentages of calcium phosphate and combeite glass-ceramic present in that formulation.

Example 7

Clinical Handling

Figure 32:
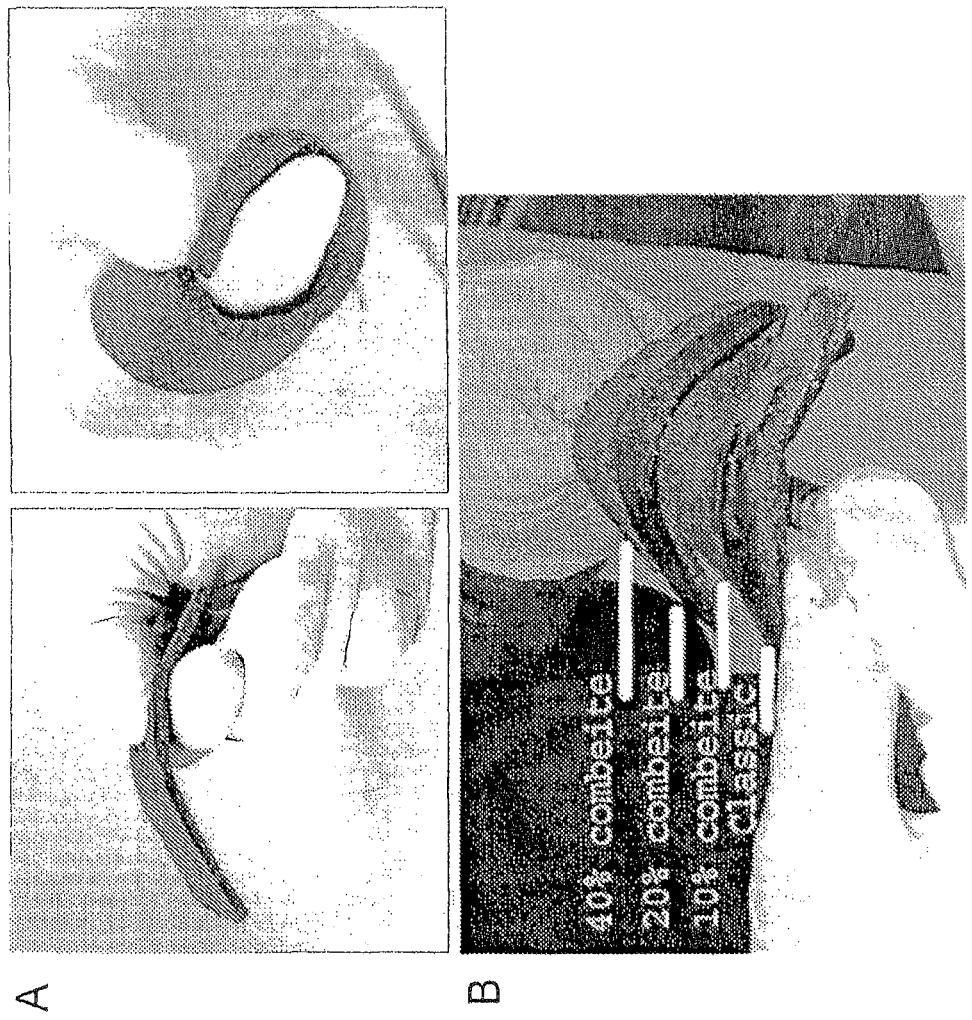
FIG. 32A shows the flexibility (when wetted) of a commercially available bone graft material (Vitoss® Foam Strip, Orthovita, Inc., Malvern, Pa.) which contains no bioactive glass.
FIG. 32B shows flexible bone graft formulations which contain no bioactive glass (classic), or 10%, 20%, or 40% combeite glass-ceramic.

Test articles containing collagen, calcium phosphate, and 80%, 40%, 20%, 10% or 0% combeite glass-ceramic were imbibed with blood and were manually surveyed for flexibility, structural integrity, and handling properties. All test formulations demonstrated the ability to wick blood, and all were flexible upon wetting (see examples in FIG. 32B; "classic" refers to 0% bioactive glass content). The samples containing up to and including 40% bioactive glass were able to hold blood under compression and were selected for further investigation.

Example 8

Samples with Glass-ceramic Particle Size <53 μm

Bone graft samples containing collagen, calcium phosphate, and 10%, 20%, or 40% combeite glass ceramic having a particle size of <53 μm were created and analyzed via SEM at various magnifications. All formulations were found to contain good distribution of all three components throughout the graft. Representative images are shown in FIG. 25.

Example 9

Samples with 45S5 Bioactive Glass Particle Size 38-250 μm

Bone graft samples containing collagen, calcium phosphate, and 10%, 20%, or 40% 45S5 bioactive glass having a particle size of 38-250 μm were created and analyzed via SEM at various magnifications. All formulations were found to contain good distribution of all three components throughout the graft. Representative images are shown in FIG. 26.

Example 10

Samples with Glass-ceramic Particle Size 90-150 μm

Bone graft samples containing collagen, calcium phosphate, and 15% combeite glass-ceramic having a particle size of 90-150 μm were created and analyzed via SEM at various magnifications. This formulation was found to result in acceptable distribution of all three components. Representative images are shown in FIG. 27.

Example 11

Bioactivity Assessment of Calcium Phosphate:Collagen:Bioactive Glass Bone Graft Substitutes (75:10:15)

Samples containing 75% calcium phosphate, 15% combeite glass ceramic with 90-150 μm particle size, and 10% collagen were prepared as strips with dimensions of 25×100×8 mm or 25×50×4 mm. Samples were cut into small rectangular bars with surface area of about 240 mm and were suspended by nylon line in about 150 mL of SBF for 3 or 7 days. Samples were analyzed via SEM and EDAX for growth of new calcium phosphate, which is indicative of bioactivity.

Figure 28:
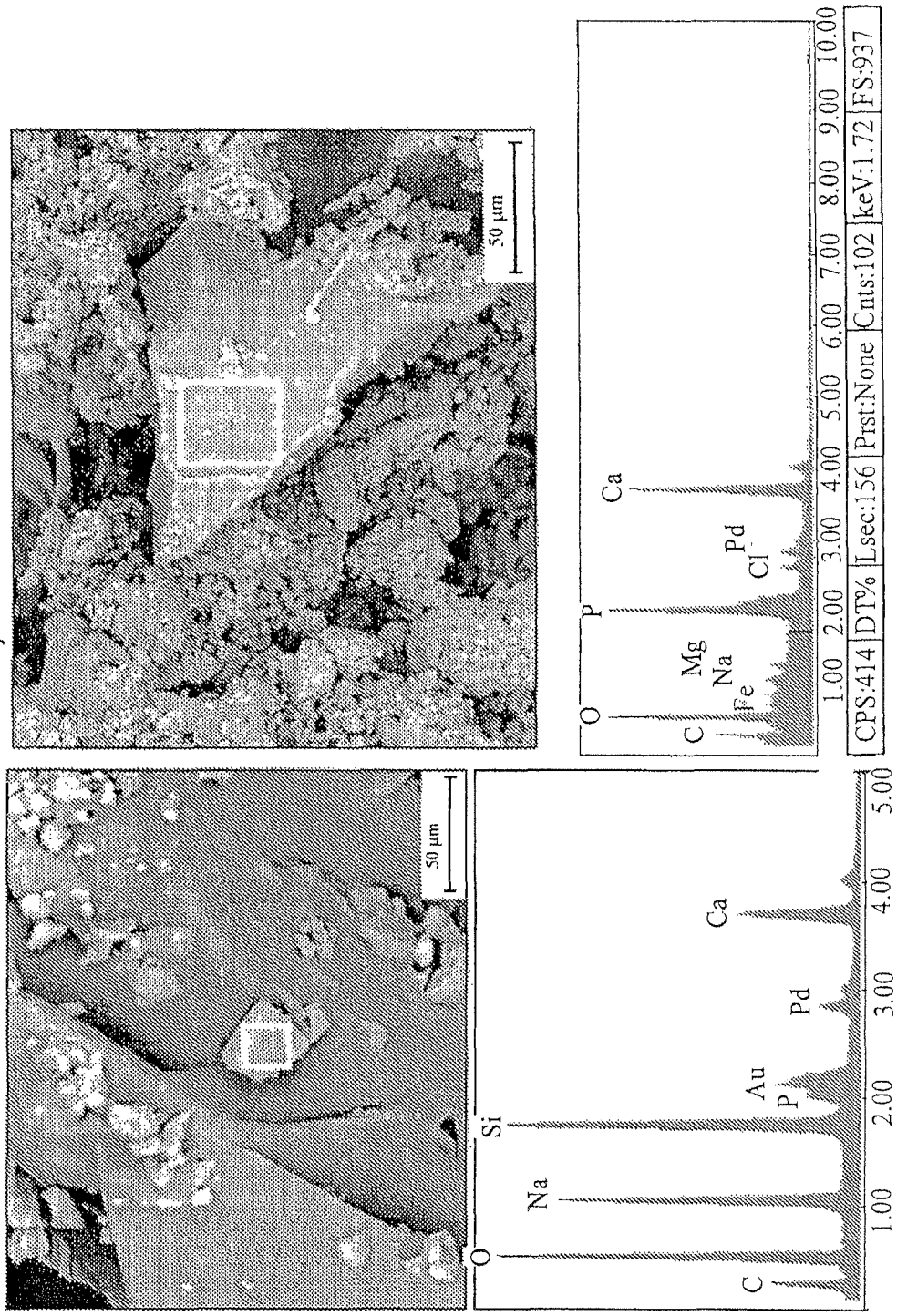
FIG. 28A shows a high magnification SEM of unreacted graft containing bioactive glass along with the EDAX spectrum corresponding with the boxed area of the image.
FIG. 28B shows a SEM of graft containing bioactive glass after 7 days in SBF along with the EDAX spectrum corresponding to the boxed area of the image, showing new calcium phosphate growth.

Via SEM and EDAX, it appeared that calcium phosphate growth had already begun by Day 3 (data not shown). Representative data from Day 7 are shown in FIGS. 28 and 29. FIG. 28B shows new calcium phosphate growth on an area of combeite glass-ceramic (boxed area on SEM image), and the corresponding EDAX spectra confirms the presence of calcium phosphate on the glass. FIG. 28A shows an unreacted control for comparison. FIG. 29B shows calcium phosphate growth throughout the surface of the bone graft substitute. The porous nature of the graft itself as well as the collagen and calcium phosphate components is evident in FIG. 29A.

Example 12

Porosity of Bone Graft Substitute

The porous character of bone grafts containing collagen; calcium phosphate having macro-, meso-, and microporosity; and 10, 20, 40, or 80% bioactive glass (combeite glass-ceramic, <53 particle size) was examined using mercury intrusion porosimetry. Shown in Table 4 is the porosity profile for each formulation. The normalized pore volume (%) is shown for each pore size range.

TABLE 4

| Porosity profile of bone grafts | | | | |
|---|---|---|---|---|
| Pore Diameter (μm) | 10% | 20% | 40% | 80% |
| 1000-350 | 5 | 5 | 3 | 4 |
| 350-100 | 10 | 8 | 8 | 12 |
| 100-10 | 61 | 66 | 65 | 69 |
| <10 | 24 | 21 | 23 | 14 |

As shown in Table 4, all formulations had similar porosity profiles and all showed high porosity. The total porosity for the formulations ranged from about 81 to about 83%.

Example 13

Assessment of Attributes of Calcium Phosphate:Collagen:Bioactive Glass Bone Graft Substitutes (75:10:15)

Samples of bioactive bone graft material containing 75% calcium phosphate (morsel size of 1-2 mm), 15% combeite glass-ceramic (90-150 μm particle size), and 10% collagen were examined with regard to desireable handling attributes.

Upon wetting with blood, the wettability ranged from about 136% to about 174% with a mean wettability of about 156%. The wettability by volume ranged from about 71% to about 90%.

The bone graft was immersed in fluid for about two minutes, was weighed, and was placed on a mesh suspended above a weigh boat, and a 500 g mass was placed on the flexible graft for about 10 seconds. The graft was then weighed again to assess retention under compressive load. The fluid retention under compressive load ranged from about 95% to about 99%, with a mean fluid retention of about 97%. The samples also handled appropriately for clinical applications and could be cut with scissors without crumbling.

Example 14

Addition of Bioactive Glass to Bone Graft Substitute Comprising Calcium Phosphate and Collagen Either 10% or 40% by weight of bioactive glass (combeite glass-ceramic with particle size of either <53 μm or 90-150 μm) was added to bone grafts (commercially available as Vitoss® Foam Pack, Orthovita, Inc., Malvern, Pa.) comprising about 80% by weight of porous calcium phosphate and about 20% by weight of collagen to form moldable composite bioactive grafts. To prepare the material, about 1.2 mL of the calcium phosphate/collagen bone graft was imbibed with about 1.3 mL of saline and was kneaded for approximately 2 minutes. The combeite glass-ceramic was then added and the composite material was kneaded for approximately 2 additional minutes before a portion was removed from roughly the center of the sample, dehydrated, and prepped for SEM analysis.

The 10% and 40%, 90-150 μm combeite glass ceramic formulations resulted in a very smooth textured sample. The 10%, <53 μm formulation was indistinguishable from graft material without glass in handling and macroscopic appearance. The 40%, <53 μm formulation was non-cohesive.

SEM analysis showed good distribution of glass throughout the graft for the formulations containing 10% of either particle size (representative SEM images shown in FIGS. 30) and 40% of 90-150 pm glass (FIG. 31A). The 40%, <53 formulation (FIG. 31B) seemed to be dominated by glass.

Example 15

In Vivo Testing of Bone Graft Materials

A bilateral canine humeral defect implant study is undertaken to evaluate bone graft material in direct contact with bone tissue. Bone remodeling, new bone formation, and implant resorption is evaluated at periodic time intervals.

The bone graft material is supplied in a form that results in a flexible graft upon wetting. (Other grafts of the present invention may be examined in the same manner.) Graft material that does not contain bioactive glass will serve as control.

The test or control material will be implanted into bilateral drill defects surgically created in the cancellous bone of the proximal humerus of 18 canines. Test article will be implanted into the drill defect of one humerus, and the control article will be implanted into the drill defect in the opposite humerus of each animal in accordance with a randomization schedule generated prior to study start. The drill defects will be approximately 10 mm in diameter and approximately 25 mm in depth. A lateral and dorso-palmar view will be obtained immediately post-operatively and all animals will be subsequently radiographed at each sacrifice time point. After the predetermined exposure period (3, 6, 12, 24, or 52 weeks), the animals will be sacrificed and the implantation sites exposed. The implant sites will be grossly observed, harvested, wrapped in a saline soaked gauze sponge and frozen at approximately −20° C. for further analysis.

Analysis of the harvested implant sites will include mechanical testing to assess the bony ingrowth and remodeling of the defect site. The tissue implant sites will also be examined using standard histology techniques well-known in the art. The extent of healing and nature of tissue contained within the defect will be characterized by the histopathological and histomorphometry evaluation.

In one embodiment, defects treated with bioactive bone graft material (material containing bioactive glass), will show improved healing. In a preferred embodiment, the rate or extent of healing in defects treated with graft material+bioactive-glass will be equal to or better than that observed in defects treated with control graft material.

Example 16

Porosity of Bone Graft Substitute

The porous character of bone grafts containing 10% collagen; 75% calcium phosphate having macro-, meso-, and microporosity (75%); and 15% bioactive glass (combeite glass-ceramic) was examined using mercury intrusion porosimetry. Shown in Table 5 is the porosity profile for two configurations of graft containing 15% combeite glass ceramic, one of dimension 25×100×4 mm (15% Thin) and one of dimension 25×50×8 mm (15% Thick). Also shown is the porosity profile for a graft without bioactive glass (0%). The normalized pore volume (%) is shown for each pore size range.

TABLE 5

| Porosity profile of bone grafts | | |
|---|---|---|
| Pore diameter (μm) | 15% Thin | 15% Thick |
| <10 | 25 | 28 |
| 10-100 | 66 | 62 |
| 100-350 | 5 | 6 |
| 350-1000 | 4 | 4 |

As shown in Table 5, both sizes of bone graft containing 15% combeite glass-ceramic had similar porosity profiles, and show macro-, meso-, and microporosity. The porosity profiles were similar to those of graft material without bioactive glass. The grafts also showed high total porosity of greater than 75%.

Example 17

Wash-away Resistance and Fluid Retention of Moldable Graft Containing Bioactive Glass About 5 cc of bone graft material comprised of porous calcium phosphate and collagen (commercially available as Vitoss® Foam Pack, Orthovita, Inc., Malvern, Pa.) was hydrated with about 4.5 cc of saline, and was kneaded to a moldable consistency. About 0.54 g of combeite glass-ceramic having particle size of 90-150 μm (about 20% based on 2.15 g dry mass of graft) was kneaded into the hydrated material.

Figure 33:
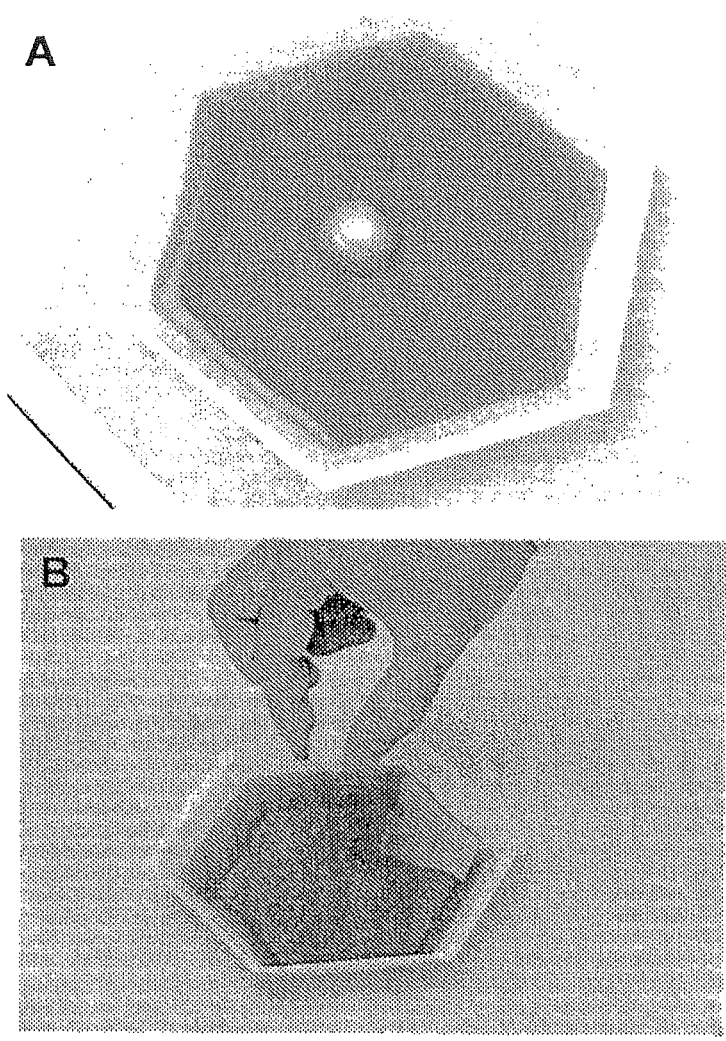
FIG. 33A & 33B show a moldable bone graft during and after, respectively, a wash-away test.

To test for wash-away resistance, composite material prepared as described was rolled into a ball and was placed in a weigh boat filled with colored saline solution for about 2 minutes (see FIG. 33). The material remained a continuous object and did not break into separate pieces, and did not swell in size substantially greater than its original dimensions.

Masses of composite material prepared as described were measured and the material was placed in a 10 cc syringe. The syringe was placed on a scale and the scale was tarred. The syringe was placed in the extrusion test jig of an Instron 4467 instrument and was subject to compression at 30 lbf. Measurement of the syringe mass after compression was used to determine the fluid retention percentage. The average fluid retention (5 samples) was about 92%, indicating that the composite material has high fluid retention properties.

Example 18

Effect of Bioactive Glass on Rate of Collagen Resorption/Stability

Samples containing calcium phosphate, collagen, and combeite glass-ceramic were cut to "thin" 10×6×4 mm samples (surface area of 248 mm2) and "thick" 5×6×8 mm samples (surface area of 236 mm2) and were suspended by nylon line in 150 ml of SBF. During a 28 day study, the 7 day thick sample fell off of its line and broke apart. Upon inspection by SEM it appeared that most of the collagen had degraded, however, some calcium phosphate coated collagen was observed. Both the thick and thin 14 day samples fell off of their lines and broke apart. The pH readings of the solution taken at day 3 were 7.6 for the thick sample and 7.53 for the thin. At day 7, the pH was 7.58 for thick and 7.54 for thin.

Further testing of "thin" 25×25×4 (surface area of 1650 mm2) and "thick" 25×13×8 (surface area of 1250 mm2) bone graft samples comprising collagen, calcium phosphate, and having the combeite glass-ceramic parameters shown in Table 6 was undertaken in PBS to examine pH alterations on a more acute time scale.

TABLE 6

Quick burst pH test

|  | Time = 0 | time = 3 hrs | time = 4 days |
|---|---|---|---|
| 0% combeite g-c | 7.32 | 7.29 | 7.28 |
| 40% <53, "thin" | 7.34 | 8.99 | 10.80 |
| 10% <53, "thin" | 7.34 | 7.84 | 9.97 |
| 15% 90-150, "thin" | 7.34 | 7.49 | 10.24 |
| 15% 90-150, "thick" | 7.34 | 7.49 | 10.38 |

The <53 μm combeite glass-ceramic caused a greater "burst" or initial pH alteration, which may be attributed to the greater surface area of the smaller particle size. However, by day 4, the formulation with the highest total glass content (40%) caused the greatest alteration in pH.

In another experiment, "thin" samples (25×25×4 mm) and "thick" samples (25×25×8 mm) of collagen and calcium phosphate graft materials containing bioactive glass of amount and type as shown in Table 7 were immersed in phosphate buffered saline (PBS) and in SBF on a shaker (1 Hz) for 12 days at 37° C.

TABLE 7

Bioactive glass content for qualitative immersion study
Glass content

0% combeite g-c
40% 38-250 45S5
40% <53 combeite g-c
15% 90-150 combeite g-c

The 15% "thick" samples in both SBF and PBS were reduced to powder as were the two 40% formulations in PBS.

In general, the bone graft materials seemed more susceptible to collagen degradation in PBS, which may be more vulnerable to pH changes. Materials with 8 mm width ("thick") appear to create higher pH and appear to be more susceptible to the degradation. While not wishing to be bound by theory, observation and testing suggests that the addition of glass alters the pH within the graft and denatures the local collagen, causing it to break down. The effect is believed to be local to the glass, and is perhaps density-dependent.

Accordingly, the rate of collagen resorption or degradation in physiologic fluids may be affected by the amount or density of bioactive glass in the graft. In general, more glass sites will cause faster breakdown and resorption of collagen.

Also provided are methods of modulating the rate of collagen resorption by adding a pH-altering material. The pH-altering material may comprise bioactive glass. Disclosed herein are methods of modulating the resorption rate of biocompatible, resorbable collagen in an implant material comprising providing implant material comprising biocompatible, resorbable collagen, adding bioactive glass to the material, and, placing the material on or in an animal. Also provided are methods of modulating the resorbability of a composition comprising collagen, comprising providing a material that has been preselected for one or more characteristics that are sufficient to alter the pH proximal to said collagen in order to alter the resorbability of the composition, and, contacting the collagen with said material. The methods may also comprise providing a material capable of altering the pH proximal to the collagen in order to alter the resorbability of the composition comprising collagen, and, contacting the collagen with said material. Also disclosed are methods of increasing the resorbability of a composition comprising collagen, comprising providing a material that has been preselected for one or more characteristics that are sufficient to raise the pH proximal to said collagen in order to effect said increased resorbability, and, contacting the collagen with the material. The change in pH proximal to the collagen may occur locally, i.e., spatially proximal to one or more portions of the collagen.

In view of the preceding description, it can be appreciated that characteristics of the bioactive glass, including, for example, the quantity and surface area of the bioactive glass can affect the rate of collagen degradation, and that these parameters can be manipulated in accordance with a desired use for the collagen-containing bone graft material. It will also be appreciated that the rate to be altered may depend on the nature of the collagen, and that the characteristics of the bioactive glass can be optimized for various forms of collagen.

It is contemplated that these methods may be applied to bone grafts as well as other collagen-containing technologies, including but not limited to wound or burn dressings, hemostatic agents, dermal implants, periodontal membranes, corneal shields, sutures, graft containment devices, cartilage replacement materials, and dura replacement materials.

With respect to a particular collagen-containing technology, the practitioner may select an optimized resorption rate. The optimal resorption rates for respective collagen-containing technologies may vary in accordance with such parameters as the rate of physiological healing, remodeling local to the site of material implantation, and other factors, and the practitioner may consider such parameters in inducing an optimized resorption rate for a particular collagen-containing technology.

Because the effect of the bioactive glass on the collagen is believed to result from pH alteration, other materials capable of producing pH changes within a collagen implant material are also suitable for achieving the result. For example, pH-altering microspheres could be used in place of the bioactive glass. It is preferred that the pH alteration occurs when the material contacts physiologic fluids. Thus, another aspect of the present invention is a method of altering the resorption rate of implant material comprising providing implant material comprising biocompatible, resorbable collagen, placing a pH altering material in admixture with the implant material, and placing the composite implant on or in the body of an animal.

There have been described presently preferred bone graft substitutes, kits containing such materials, and methods for their use. While the present invention has been particularly shown and described with reference to the presently preferred embodiments thereof, it is understood that the invention is not limited to the embodiments or examples specifically disclosed herein. It will be appreciated that methods of treating bony defects are foreseen by the embodiments of the present invention. Contemplated herein is a method for restoring or repairing bone in an animal comprising accessing a site to be restored; and implanting into a bony space a bone graft material comprising biocompatible, resorbable collagen, the oxidation-reduction reaction product of at least one metal cation, at least one oxidizing agent, and at least one oxidizable precursor anion; and bioactive glass.

The graft material used in this method may be chosen by one skilled in the art from among those disclosed in the present application. Numerous changes and modifications may be made to the preferred embodiments of the invention, and such changes and modifications may be made without departing from the spirit of the invention. It is therefore intended that the appended claims cover all such equivalent variations as they fall within the true spirit and scope of the invention.

The invention claimed is:

1. A kit for the preparation of a bone graft comprising:
   (a) a bone graft material comprising a blend of resorbable collagen and resorbable calcium phosphate; and
   (b) a separate container that contains bioactive glass therein.

2. The kit of claim 1, wherein the bioactive glass comprises combeite glass-ceramic, 45S5 glass, 45S5 glass-ceramic, 58S5 glass, S53P4 glass, apatite-wollastonite glass, or apatite-wollastonite glass-ceramic.

3. The kit of claim 1, wherein the bioactive glass has a particle size of less than 150 μm.

4. The kit of claim 1, wherein the bioactive glass is provided in a unit dose amount.

5. The kit of claim 1, wherein the bioactive glass is combeite.

6. The kit of claim 1, wherein the calcium phosphate is beta-TCP.

7. The kit of claim 1, wherein the bone graft material has micro-, meso-, and macroporosity.

8. The kit of claim 1, wherein the bone graft material is flexible, moldable, or flowable upon wetting.

9. The kit of claim 1, wherein the blend is homogeneous.

10. The kit of claim 1, wherein the bone graft comprises up to about 20% by weight of collagen.

11. The kit of claim 1, wherein the bone graft comprises up to about 15% by weight of collagen.

12. The kit of claim 1, wherein the bone graft comprises up to about 10% by weight of collagen.

13. The kit of claim 1, wherein the bioactive glass is present in an amount such that when the bioactive glass is blended with the bone graft material to form the bone graft, the bone graft comprises up to about 40% by weight of bioactive glass.

14. The kit of claim 1, wherein the bioactive glass is present in an amount such that when the bioactive glass is blended with the bone graft material to form the bone graft, the bone graft comprises up to about 20% by weight of bioactive glass.

15. The kit of claim 1, wherein the bioactive glass is present in an amount such that when the bioactive glass is blended with the bone graft to form the bone graft, the bone graft comprises up to about 15% by weight of bioactive glass.

16. A method for restoring or repairing bone in a mammal comprising:
   providing a biocompatible bone graft material of claim 1;
   incorporating resorbable bioactive glass into the bone graft material to form a bone graft comprising calcium phosphate, collagen, and bioactive glass; and
   placing the bone graft into a bony space.

17. The method of claim 16, wherein the bioactive glass comprises combeite glass-ceramic, 45S5 glass, 45S5 glass-ceramic, 58S5 glass, S53P4 glass, apatite-wollastonite glass, or apatite-wollastonite glass-ceramic.

18. The method of claim 16, further comprising wetting the bone graft material with a biologically compatible fluid prior to placing the bone graft into the bony space.

19. The method of claim 18, wherein the biologically compatible fluid is bone marrow aspirate.

20. The method of claim 16, wherein the bone graft material has micro-, meso-, and macroporosity.

* * * * *